(12) United States Patent
Chapman et al.

(10) Patent No.: US 7,442,839 B2
(45) Date of Patent: Oct. 28, 2008

(54) PHENETHANOLAMINE DERIVATIVE FOR THE TREATMENT OF RESPIRATORY DISEASES

(75) Inventors: Alan Michael Chapman, Tonbridge (GB); Stephen Barry Guntrip, Stevenage (GB); Brian Edgar Looker, Stevenage (GB); Panayiotis Alexandrou Procopiou, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 118 days.

(21) Appl. No.: 10/532,869

(22) PCT Filed: Oct. 24, 2003

(86) PCT No.: PCT/EP03/12035

§ 371 (c)(1),
(2), (4) Date: Apr. 5, 2006

(87) PCT Pub. No.: WO2004/037773

PCT Pub. Date: May 6, 2004

(65) Prior Publication Data

US 2006/0205794 A1    Sep. 14, 2006

(30) Foreign Application Priority Data

Oct. 28, 2002    (GB) .................................. 0225022.3
Oct. 28, 2002    (GB) .................................. 0225028.0

(51) Int. Cl.
| | | |
|---|---|---|
| C07C 317/22 | (2006.01) | |
| C07C 323/19 | (2006.01) | |
| C07D 213/66 | (2006.01) | |
| C07D 215/22 | (2006.01) | |
| C07D 215/26 | (2006.01) | |
| C07D 261/10 | (2006.01) | |
| C07D 309/40 | (2006.01) | |
| C07D 319/08 | (2006.01) | |
| C07D 263/22 | (2006.01) | |
| A61K 31/145 | (2006.01) | |
| A61K 31/435 | (2006.01) | |
| A61P 11/00 | (2006.01) | |

(52) U.S. Cl. ....................... 564/361; 546/329; 548/247; 549/417; 514/352; 514/378; 514/460; 514/653

(58) Field of Classification Search ........................ None
See application file for complete search history.

(56) References Cited

U.S. PATENT DOCUMENTS

| | | | |
|---|---|---|---|
| 2,918,408 A | 12/1959 | Biel | |
| 4,778,054 A | 10/1988 | Newell et al. | |
| 4,811,731 A | 3/1989 | Newell et al. | |
| 5,035,237 A | 7/1991 | Newell et al. | |
| 5,552,438 A | 9/1996 | Christensen, IV | |
| 5,590,645 A | 1/1997 | Davies et al. | |
| 5,860,419 A | 1/1999 | Davies et al. | |
| 5,873,360 A | 2/1999 | Davies et al. | |
| 5,998,428 A | 12/1999 | Barnette et al. | |
| 6,321,747 B1 | 11/2001 | Dmitrovic et al. | |

FOREIGN PATENT DOCUMENTS

| | | |
|---|---|---|
| DE | 35138885 | 10/1985 |
| DE | 3524990 | 1/1986 |
| EP | 162576 | 11/1985 |
| EP | 220054 | 4/1987 |
| EP | 0947498 | 10/1999 |
| GB | 2064336 | 6/1981 |
| GB | 2129691 | 5/1984 |
| GB | 2140800 | 12/1984 |
| GB | 2159151 | 11/1985 |
| GB | 2165542 | 4/1986 |
| GB | 2169265 | 7/1986 |
| GB | 2178965 | 2/1987 |
| GB | 2230523 | 10/1990 |
| GB | 2242134 | 9/1991 |
| WO | WO 98/29405 | 7/1998 |
| WO | WO 99/16766 | 4/1999 |
| WO | WO 99/47505 | 9/1999 |
| WO | WO 00/51599 | 9/2000 |
| WO | WO 01/13953 | 3/2001 |
| WO | WO 01/96278 | 12/2001 |
| WO | WO 02/066422 | 8/2002 |
| WO | WO 03/024439 | 3/2003 |
| WO | WO 2004/037807 | 5/2004 |

OTHER PUBLICATIONS

Augstein et al., "Aryloxyalkylaminoguanidines. Their synthesis and biological properties," *J. Med. Chem* 10:391-400 (1967).
Connon et al., "Recent developments in olefin cross-metathesis," *Angew. Chem. Int. Ed.* 42(17):1900-1923 (Apr. 2003).

(Continued)

*Primary Examiner*—Brian J Davis
(74) *Attorney, Agent, or Firm*—Robert J. Smith

(57) ABSTRACT

The present invention relates to novel compounds of formula (I),

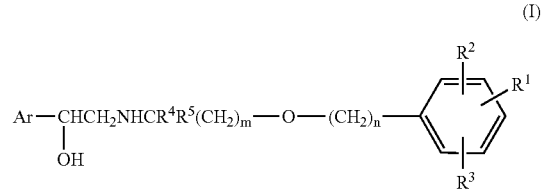

to a process for their manufacture, to pharmaceutical compositions containing them, and to their use in therapy, in particular their use in the prophylaxis and treatment of respiratory diseases.

22 Claims, 5 Drawing Sheets

OTHER PUBLICATIONS

Fuji et al., "Novel phosphodiesterase 4 inhibitor T-440 reverses and prevents human bronchial contraction induced by allergen," *The Journal of Pharmacology and Experimental Theapeutics* 284(1):162-169 (1998).

Hett et al., "Large-scale synthesis of enantio- and diastereomerically pure (R,R)-formoterol," *Organic Process Research & Development* 2(2):96-99 (Mar. 1998).

Kaiser et al., "Adrenergic agents. 4. Substituted phenoxypropanolamine derivatives as potential β-adrenergic agonists," *J. Med. Chem.* 20(5):687-692 (May 1977).

Landells et al., "Oral administration of the phosphodiesterase (PED)4 inhibitor, V11294A inhibits ex-vivo agonist-induced cell activation," *Eur Resp J.* 12 (Suppl. 28):Abst. P2393 CAS reference No. 162401-32-3 (Sep. 19-23, 1998).

LeClerc et al., "Synthesis and structure-activity relationships among α-adrenergic receptor agonists of the phenylethanolamine type," *J. Med. Chem.* 23(7):738-744 (1980).

Sonesson et al., "An efficient synthesis of the novel dopamine autoreceptor antagonist S-(-)-OSU6162, via palladium catalyzed cross-coupling reaction," *Tet. Letts.* 35(48):9063-9066 (Nov. 1994).

PHENETHANOLAMINE DERIVATIVE FOR THE TREATMENT OF RESPIRATORY DISEASES

CROSS-REFERENCE TO RELATED APPLICATIONS

This application is filed under 35 U.S.C. 371 as the United States National Phase Application of International Application No. PCT/EP2003/012035 filed Oct. 24, 2003 claiming priority from UK Patent Application Nos. 0225022.3 dated Oct. 28, 2002 and 02255028.0 dated Oct. 28, 2002.

The present invention is concerned with phenethanolamine derivatives, processes for their preparation, compositions containing them and their use in medicine, particularly in the prophylaxis and treatment of respiratory diseases.

Certain phenethanolamine compounds are known in the art as having selective stimulant action at $\beta_2$-adrenoreceptors and therefore having utility in the treatment of bronchial asthma and related disorders. Thus GB 2 140 800 describes phenethanolamine compounds including 4-hydroxy-$\alpha^1$-[[[6-(4-phenylbutoxy)hexyl]amino]methyl]-1,3-benzene-dimethanol 1-hydroxy-2-naphthalenecarboxylate (salmeterol xinafoate) which is now used clinically in the treatment of such medical conditions.

Although salmeterol and the other commercially available $\beta_2$-adrenoreceptor agonists are effective bronchodilators, the duration of action is approximately 12 hours, hence twice daily dosing is often required. There is therefore a clinical need for compounds having potent and selective stimulant action at $\beta_2$-adrenoreceptors and having an advantageous profile of action.

According to the present invention, there is provided a compound of formula (I)

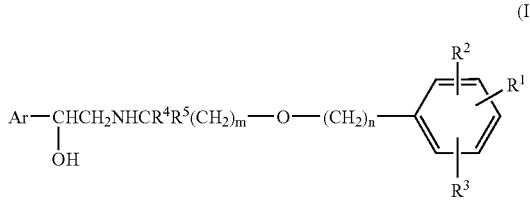

or a salt, solvate, or physiologically functional derivative thereof, wherein:

m is an integer of from 2 to 8;

n is an integer of from 3 to 11, preferably from 3 to 7;

with the proviso that m+n is 5 to 19, preferably 5 to 12;

$R^1$ is $SR^6$, $SOR^6$, or $SO_2R^6$, wherein $R^6$ is a $C_{3-7}$cycloalkyl or $C_{3-7}$cycloalkenyl group;

$R^2$ and $R^3$ are independently selected from hydrogen, $C_{1-6}$alkyl, $C_{1-6}$alkoxy, halo, phenyl, and $C_{1-6}$haloalkyl;

$R^4$ and $R^5$ are independently selected from hydrogen and $C_{1-4}$alkyl with the proviso that the total number of carbon atoms in $R^4$ and $R^5$ is not more than 4;

Ar is a group selected from

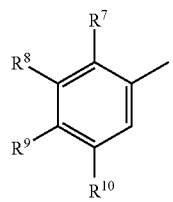

(a)

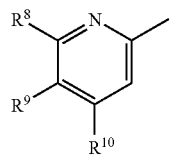

(b)

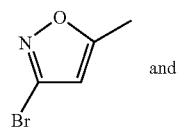

and (c)

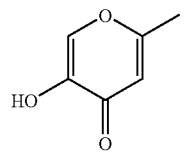

(d)

wherein $R^8$ represents hydrogen, halogen, —$(CH_2)_qOR^{11}$, —$NR^{11}C(O)R^{12}$, —$NR^{11}SO_2R^{12}$, —$SO_2NR^{11}R^{12}$, —$NR^{11}R^{12}$, —$OC(O)R^{13}$ or $OC(O)NR^{11}R^{12}$, and $R^7$ represents hydrogen, halogen, or $C_{1-4}$ alkyl;

or $R^8$ represents —$NHR^{14}$ and $R^7$ and —$NHR^{14}$ together form a 5- or 6-membered heterocyclic ring;

$R^9$ represents hydrogen, halogen, —$OR^{11}$ or —$NR^{11}R^{12}$;

$R^{10}$ represents hydrogen, halogen, haloC$_{1-4}$ alkyl, —$OR^{11}$, —$NR^{11}R^{12}$, —$OC(O)R^{13}$ or $OC(O)NR^{11}R^{12}$;

$R^{11}$ and $R^{12}$ each independently represents hydrogen or $C_{1-4}$ alkyl, or in the groups —$NR^{11}R^{12}$, —$SO_2NR^{11}R^{12}$ and —$OC(O)NR^{11}R^{12}$, $R^{11}$ and $R^{12}$ independently represent hydrogen or $C_{1-4}$ alkyl or together with the nitrogen atom to which they are attached form a 5-, 6- or 7-membered nitrogen-containing ring, $R^{13}$ represents an aryl (eg phenyl or naphthyl) group which may be unsubstituted or substituted by one or more substituents selected from halogen, $C_{1-4}$ alkyl, hydroxy, $C_{1-4}$ alkoxy or halo $C_{1-4}$ alkyl; and q is zero or an integer from 1 to 4.

In a particular embodiment, the present invention provides compounds of formula (I) and salts, solvates and physiologically functional derivatives thereof, wherein formula (I) is as defined hereinabove, except that $R^8$ does not represent hydrogen.

In the compounds of formula (I) the group $R^1$ is preferably attached to the meta-position relative to the —O—$(CH_2)_n$— link.

$R^1$ preferably represents $SOR^6$ or $SO_2R^6$, most preferably $SO_2R^6$.

$R^6$ preferably represents $C_{3-7}$cycloalkyl, most preferably cyclopentyl.

$R^4$ and $R^5$ are preferably independently selected from hydrogen and methyl, more preferably $R^4$ and $R^5$ are both hydrogen.

m is suitably 4, 5, or 6, and n is suitably 3, 4, 5 or 6. Preferably m is 5 or 6 and n is 3 or 4, such that m+n is 8, 9 or 10, preferably 9.

In the compounds of formula (I) the group Ar is preferably selected from groups (a) and (b) above. In said groups (a) and (b), when $R^8$ represents halogen this is preferably chlorine or fluorine. $R^{11}$ and $R^{12}$ preferably each independently represent hydrogen or methyl. $R^{13}$ preferably represents substituted phenyl. The integer q preferably represents zero or 1. Thus for example —$(CH_2)_q OR^{11}$ preferably represents OH or —$CH_2OH$;

$NR^{11}C(O)R^{12}$ preferably represents —NHC(O)H;

—$SO_2NR^{11}R^{12}$ preferably represents —$SO_2NH_2$ or $SO_2NHCH_3$;

$NR^{11}R^{12}$ preferably represents —$NH_2$;

—$OC(O)R^{13}$ preferably represents substituted benzoyloxy eg. OC(O)—$C_6H_4$—($p$—$CH_3$); and —OC(O)N $R^{11}$ $R^{12}$ preferably represents $OC(O)N(CH_3)_2$.

When $R^8$ represents $NHR^{14}$ and together with $R^7$ forms a 5- or 6-membered heterocyclic ring —$NHR^{14}$—$R^7$-preferably represents a group:

—NH—CO—$R^{15}$-where $R^{15}$ is an alkyl, alkenyl or alkyloxy moiety;

—NH—$SO_2R^{16}$-where $R^{16}$ is an alkyloxy moiety;

—NH—$R^{17}$-where $R^{17}$ is an alkyl or alkenyl moiety optionally substituted by $COOR^{18}$ where $R^{18}$ is $C_{1-4}$ alkyl; or

—NH—CO—S—;

wherein said alkyl, and alkenyl groups and moieties contain 1 or 2 carbon atoms.

Particularly preferred groups (a) and (b) may be selected from the following groups (i) to (xxi):

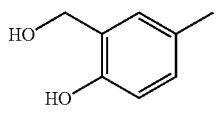
(i)

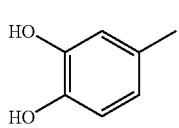
(ii)

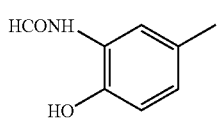
(iii)

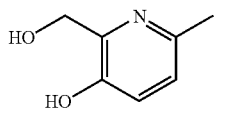
(iv)

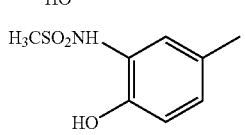
(v)

-continued

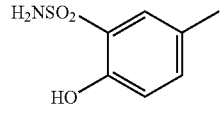
(vi)

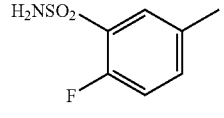
(vii)

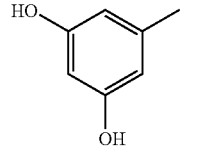
(viii)

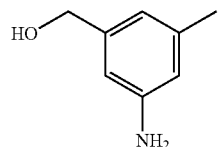
(ix)

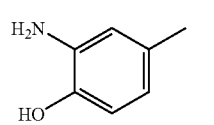
(x)

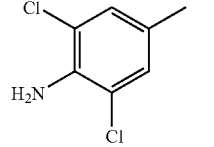
(xi)

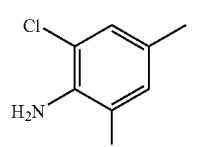
(xii)

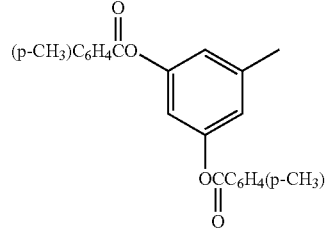
(xiii)

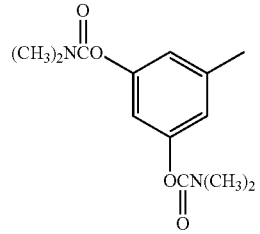
(xiv)

-continued

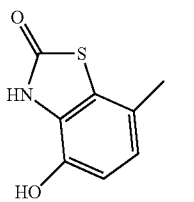
(xv)

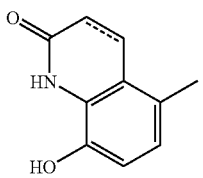
(xvi)

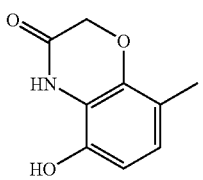
(xvii)

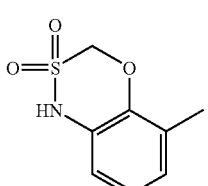
(xviii)

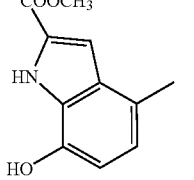
(xix)

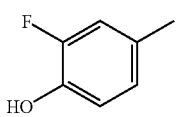
(xx)

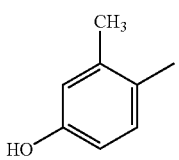
(xxi)

wherein the dotted line in (xvi) and (xix) denotes an optional double bond.

Most preferably Ar represents a group (i).

In a particularly preferred embodiment the present invention provides a compound of formula (Ia)

(Ia)

HOCH$_2$—, HO—, —CHCH$_2$NHCR$^4$R$^5$(CH$_2$)$_m$—O—(CH$_2$)$_n$—, R$^2$, R$^1$, R$^3$, OH or a salt, solvate, or physiologically functional derivative thereof, wherein:

m is an integer of from 2 to 8;
n is an integer of from 3 to 11, preferably from 3 to 7;
with the proviso that m+n is 5 to 19, preferably 5 to 12;
R$^1$ is SR$^6$, SOR$^6$, or SO$_2$R$^6$,
  wherein R$^6$ is a C$_{3-7}$cycloalkyl or C$_{3-7}$cycloalkenyl group;
R$^2$ and R$^3$ are independently selected from hydrogen, C$_{1-6}$alkyl, C$_{1-6}$alkoxy, halo, phenyl, and C$_{1-6}$haloalkyl; and
R$^4$ and R$^5$ are independently selected from hydrogen and C$_{1-4}$alkyl with the proviso that the total number of carbon atoms in R$^4$ and R$^5$ is not more than 4.

In the compounds of formula (Ia) the group R$^1$ is preferably attached to the meta-position relative to the —O—(CH$_2$)$_n$— link.

R$^1$ preferably represents SOR$^6$ or SO$_2$R$^6$, most preferably SO$_2$R$^6$.

R$^6$ preferably represents C$_{3-7}$ cycloalkyl, most preferably cyclopentyl.

R$^4$ and R$^5$ are preferably independently selected from hydrogen and methyl, more preferably R$^4$ and R$^5$ are both hydrogen.

m is suitably 4, 5, or 6, and n is suitably 2, 3, 4, 5 or 6. Preferably m is 5 or 6 and n is 3 or 4, such that m+n is 8, 9 or 10, preferably 9.

Preferred compounds of formulae (I) and (Ia) include:
4{(1R)-2-[(6-{4-[3-(Cyclopentylsulfinyl)phenyl]butoxy}hexyl)amino]-1-hydroxyethyl)-2-(hydroxymethyl)phenol;
4-{(1R)-2-[(6-{4-[3-(Cyclopentylsulfinyl)phenyl]butoxy}hexyl)amino]-1-hydroxyethyl}-2-(hydroxymethyl)phenol (Isomer 1);
4{(1R)-2-[(6-{4-[3-(Cyclopentylsulfinyl)phenyl]butoxy}hexyl)amino]-1-hydroxyethyl}-2-(hydroxymethyl)phenol (Isomer 2);
4{(1R)-2-[(6-{4-[3(Cyclopentylsulfonyl)phenyl]butoxy}hexyl)amino]-1-hydroxyethyl}-2-(hydroxymethyl)phenol;
4{(1R)-2-[(6-{4-[4-(Cyclopentylsulfonyl)phenyl]butoxy}hexyl)amino]-1-hydroxyethyl}-2-(hydroxymethyl)phenol;
4-((1R)-2-{[6-({4-[3-(Cyclohexylsulfonyl)phenyl]butyl}oxy)hexyl]amino}-1-hydroxyethyl)-2-(hydroxymethyl)phenol;
4-((1R)-2-{[6-({4-[3-(3-Cyclopenten-1-ylsulfonyl)phenyl]butyl}oxy)hexyl]amino}-1-hydroxyethyl)-2-(hydroxymethyl)phenol;
4-((1R)-2-{[6-({5-[3-(Cyclopentylsulfonyl)phenyl]pentyl}oxy)hexyl]amino}-1-hydroxyethyl)-2-(hydroxymethyl)phenol;
4-((1R)-2-{[7-({3-[3-(Cyclopentylsulfonyl)phenyl]propyl}oxy)heptyl]amino}-1-hydroxyethyl)-2-(hydroxymethyl)phenol;
4-((1R)-2-{[6-({4-[3-(Cyclopentylsulfonyl)-5-methylphenyl]butyl}oxy)hexyl]amino}-1-hydroxyethyl)-2-(hydroxymethyl)phenol;
N-[5-((1R)-2-{[6-({4-[3-(Cyclopentylsulfonyl)phenyl]butyl}oxy)hexyl]amino}-1-hydroxyethyl)-2-hydroxyphenyl]methanesulfonamide;
4-((1R)-2-{[6-({4-[3-(Cyclopentylsulfonyl)phenyl]butyl}oxy)hexyl]amino}-1-hydroxyethyl)-2-fluorophenol;
6-{2-[(6-{4-[3-(Cyclopentylsulfonyl)phenyl]butoxy}hexyl)amino]-1-hydroxyethyl}-2-(hydroxymethyl)pyridin-3-ol;
5{(1R)-2-[(6-{4-[3(Cyclopentylsulfonyl)phenyl]butoxy}hexyl)amino]-1-hydroxyethyl}-8-hydroxy-3,4-dihydroquinolin-2(1H)-one;

5-{(1R)-2-[(6-{4-[3(Cyclopentylsulfonyl)phenyl]
butoxy}hexyl)amino]-1-hydroxyethyl}-2-hydroxyphe-
nylformamide;
and salts, solvates, and physiologically functional derivatives
thereof.

A particularly preferred compound of formula (I) is:
4-{(1R)-2-[(6-{4-[3-(Cyclopentylsulfonyl)phenyl]
butoxy}hexyl)amino]-1-hydroxyethyl}-2-(hydroxym-
ethyl)phenol;
and salts, solvates, and physiologically functional derivatives
thereof.

It will be appreciated that the compounds of formula (I) and (Ia) include two asymmetric centres, namely the carbon atom of the

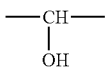

group and, when $R^1$ represents $SOR^6$, at the sulphur atom of the sulphoxide group The compounds may therefore exist in four different isomeric forms. The present invention includes both (S) and (R) enantiomers at both chiral centres either in substantially pure form or admixed in any proportions.

Similarly, where $R^4$ and $R^5$ are different groups, the carbon atom to which they are attached is an asymmetric centre and the present invention includes both (S) and (R) enantiomers at this centre either in substantially pure form or admixed in any proportions.

Thus the compounds of formula (I) and (Ia) include all enantiomers and diastereoisomers as well as mixtures thereof in any proportions.

Salts and solvates of compounds of formula (I) and (Ia) which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of formula (I) and (Ia) and their pharmaceutically acceptable salts, solvates, and physiologically functional derivatives.

By the term "physiologically functional derivative" is meant a chemical derivative of a compound of formula (I) or (Ia) having the same physiological function as the parent compound of formula (I) or (Ia) for example, by being convertible in the body thereto. According to the present invention, examples of physiologically functional derivatives include esters.

Suitable salts according to the invention include those formed with both organic and inorganic acids or bases. Pharmaceutically acceptable acid addition salts include those formed from hydrochloric, hydrobromic, sulphuric, citric, tartaric, phosphoric, lactic, pyruvic, acetic, trifluoroacetic, triphenylacetic, sulphamic, sulphanilic, succinic, oxalic, fumaric, maleic, malic, glutamic, aspartic, oxaloacetic, methanesulphonic, ethanesulphonic, arylsulphonic (for example p-toluenesulphonic, m-toluenesulphonic, benzenesulphonic, 4-chlorobenzenesulphonic, 4-bromobenzenesulphonic, 4-phenylbenzenesulphonic, naphthalenesulphonic or naphthalenedisulphonic), salicylic, glutaric, gluconic, tricarballylic, cinnamic, substituted cinnamic (for example, phenyl, methyl, cynao, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic) and isethionic acids. Pharmaceutically acceptable base salts include ammonium salts, alkali metal salts such as those of sodium and potassium, alkaline earth metal salts such as those of calcium and magnesium and salts with organic bases such as dicyclohexyl amine and N-methyl-D-glucamine.

Advantageously, preferred compounds of the invention such as 4-{(1R)-2-[(6-{4-[3-(cyclopentylsulfonyl)phenyl] butoxy}hexyl)amino]-1-hydroxyethyl}-2-(hydroxymethyl) phenol, are provided in the form of a crystalline salt, for example selected from those exemplified in the experimental section below. Particularly preferred salts include benzenesulfonate derivatives such as the p-toluenesulfonate, m-toluenesulfonate, 4-chlorobenzenesulfonate, 4-bromobenzenesulfonate, 4-phenylbenzenesulfonate and naphthalene-2-sulfonate salts.

Pharmaceutically acceptable esters of the compounds of formula (I) and (Ia) may have a hydroxyl group converted to a $C_{1-6}$ alkyl, aryl, aryl $C_{1-6}$ alkyl, or amino acid ester.

As mentioned above, the compounds of formula (I) and (Ia) are selective $\beta_2$-adrenoreceptor agonists as demonstrated using functional or reporter gene readout from cell lines transfected with human beta-adrenoreceptors, or membranes derived from these cells, as described below. Compounds according to the present invention also have the potential to combine long duration of effect with rapid onset of action. Furthermore, certain compounds have shown an improved therapeutic index in animal models relative to existing long-acting $\beta_2$-agonist bronchodilators. As such, compounds of the invention may be suitable for once-daily administration. Preferred compounds of the invention also exhibit relatively low absorption in the rat following oral administration. Whilst the compounds of the invention are principally intended for administration by inhalation, a certain proportion of the dose, which can be as much as 80%, may be swallowed by the patient, with the potential for unwanted systemic effects. Low oral absorption is therefore a desirable property for compounds of the invention.

Compounds of formula (I) and (Ia) and their pharmaceutically acceptable salts, solvates, and physiologically functional derivatives have use in the prophylaxis and treatment of clinical conditions for which a selective $\beta_2$-adrenoreceptor agonist is indicated. Such conditions include diseases associated with reversible airways obstruction such as asthma, chronic obstructive pulmonary diseases (COPD) (e.g. chronic and wheezy bronchitis, emphysema), respiratory tract infection and upper respiratory tract disease (e.g. rhinitis, including seasonal and allergic rhinitis).

Other conditions which may be treated include premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

Accordingly, the present invention provides a method for the prophylaxis or treatment of a clinical condition in a mammal, such as a human, for which a selective $\beta_2$-adrenoreceptor agonist is indicated, which comprises administration of a therapeutically effective amount of a compound of formula (I) or (Ia) or a pharmaceutically acceptable salt, solvate, or physiologically functional derivative thereof. In particular, the present invention provides such a method for the prophylaxis or treatment of a disease associated with reversible airways obstruction such as asthma, chronic obstructive pulmonary disease (COPD), respiratory tract infection or upper respiratory tract disease. In a further aspect the present invention provides such a method for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

In the alternative, there is also provided a compound of formula (I) or (Ia) or a pharmaceutically acceptable salt, solvate, or physiologically functional derivative thereof for use in medical therapy, particularly, for use in the prophylaxis or treatment of a clinical condition in a mammal, such as a human, for which a selective $\beta_2$-adrenoreceptor agonist is indicated. In particular, there is provided a compound of formula (I) or (Ia) or a pharmaceutically acceptable salt, solvate, or physiologically functional derivative thereof for the prophylaxis or treatment of a disease associated with reversible airways obstruction such as asthma, chronic obstructive pulmonary disease (COPD), respiratory tract infection or upper respiratory tract disease. In a further aspect, there is provided a compound of formula (I) or (Ia) or a pharmaceutically acceptable salt, solvate, or physiologically functional derivative thereof for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) or muscle wasting disease.

The present invention also provides the use of a compound of formula (I) or (Ia) or a pharmaceutically acceptable salt, solvate, or physiologically functional derivative thereof in the manufacture of a medicament for the prophylaxis or treatment of a clinical condition for which a selective $\beta_2$-adrenoreceptor agonist is indicated, for example a disease associated with reversible airways obstruction such as asthma, chronic obstructive pulmonary disease (COPD), respiratory tract infection or upper respiratory tract disease.

In a further aspect, there is provided a compound of formula (I) or (Ia) or a pharmaceutically acceptable salt, solvate, or physiologically functional derivative thereof in the manufacture of a medicament for the prophylaxis or treatment of a clinical condition selected from premature labour, depression, congestive heart failure, skin diseases (e.g. inflammatory, allergic, psoriatic, and proliferative skin diseases), conditions where lowering peptic acidity is desirable (e.g. peptic and gastric ulceration) and muscle wasting disease.

The amount of a compound of formula (I) or (Ia) or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The compounds of the invention may be administered by inhalation at a dose of from 0.0005 mg to 10 mg, preferably 0.005 mg to 0.5 mg. eg. 0.05 mg to 0.5 mg. The dose range for adult humans is generally from 0.0005 mg to 10 mg per day and preferably 0.01 mg to 1 mg per day, most preferrably 0.05 mg to 0.5 mg.

While it is possible for the compound of formula (I) or (Ia) or a pharmaceutically acceptable salt, solvate, or physiologically functional derivative thereof to be administered alone, it is preferable to present it as a pharmaceutical formulation.

Accordingly, the present invention further provides a pharmaceutical formulation comprising a compound of formula (I) or (Ia) or a pharmaceutically acceptable salt, solvate, or physiologically functional derivative thereof, and a pharmaceutically acceptable carrier or excipient, and optionally one or more other therapeutic ingredients.

Hereinafter, the term "active ingredient" means a compound of formula (I) or (Ia) or a pharmaceutically acceptable salt, solvate, or physiologically functional derivative thereof.

The formulations include those suitable for oral, parenteral (including subcutaneous, intradermal, intramuscular, intravenous and intraarticular), inhalation (including fine particle dusts or mists which may be generated by means of various types of metered dose pressurised aerosols, nebulisers or insufflators), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described.

Dry powder compositions for topical delivery to the lung by inhalation may, for example, be presented in capsules and cartridges of for example gelatine, or blisters of for example laminated aluminium foil, for use in an inhaler or insufflator. Powder blend formulations generally contain a powder mix for inhalation of the compound of the invention and a suitable powder base (carrier/diluent/excipient substance) such as mono-, di or poly-saccharides (eg. lactose or starch). Use of lactose is preferred.

Each capsule or cartridge may generally contain between 20 µg-10 mg of the compound of formula (I) or (Ia) optionally in combination with another therapeutically active ingredient. Alternatively, the compound of the invention may be presented without excipients. Packaging of the formulation may be suitable for unit dose or multi-dose delivery. In the case of multi-dose delivery, the formulation can be pre-metered (eg as in Diskus, see GB 2242134, U.S. Pat. Nos. 6,632, 666, 5,860,419, 5,873,360 and 5,590,645 or Diskhaler, see GB 2178965, 2129691 and 2169265, U.S. Pat. Nos. 4,778, 054, 4,811,731, 5,035,237, the disclosures of which are hereby incorporated by reference) or metered in use (eg as in Turbuhaler, see EP 69715 or in the devices described in U.S. Pat. No. 6,321,747 the disclosures of which are hereby incorporated by reference). An example of a unit-dose device is Rotahaler (see GB 2064336 and U.S. Pat. No. 4,353,656, the disclosures of which are hereby incorporated by reference). The Diskus inhalation device comprises an elongate strip formed from a base sheet having a plurality of recesses spaced along its length and a lid sheet hermetically but peelably sealed thereto to define a plurality of containers, each container having therein an inhalable formulation containing a compound of formula (I) or (Ia) preferably combined with lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Spray compositions for topical delivery to the lung by inhalation may for example be formulated as aqueous solutions or suspensions or as aerosols delivered from pressurised packs, such as a metered dose inhaler, with the use of a suitable liquefied propellant. Aerosol compositions suitable for inhalation can be either a suspension or a solution and generally contain the compound of formula (I) or (Ia) optionally in combination with another therapeutically active ingredient and a suitable propellant such as a fluorocarbon or hydrogen-containing chlorofluorocarbon or mixtures thereof, particularly hydrofluoroalkanes, e.g. dichlorodifluoromethane, trichlorofluoromethane, dichlorotetra-fluoroethane, especially 1,1,1,2-tetrafluoroethane, 1,1,1,2,3,3,3-heptafluoro-n-propane or a mixture thereof. Carbon dioxide or other suitable gas may also be used as propellant. The aerosol composition may be excipient free or may optionally contain additional formulation excipients well known in the art such as surfactants eg oleic acid or lecithin and cosolvents eg ethanol. Pressurised formulations will generally be retained in a canister (eg an aluminium canister) closed with a valve (eg a metering valve) and fitted into an actuator provided with a mouthpiece.

Medicaments for administration by inhalation desirably have a controlled particle size. The optimum particle size for inhalation into the bronchial system is usually 1-10 µm, preferably 2-5 µm. Particles having a size above 20 µm are generally too large when inhaled to reach the small airways. To achieve these particle sizes the particles of the active ingredient as produced may be size reduced by conventional means eg by micronisation. The desired fraction may be separated out by air classification or sieving. Preferably, the particles will be crystalline. When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 µm and not less than 15% will have a MMD of less than 15 µm.

Intranasal sprays may be formulated with aqueous or non-aqueous vehicles with the addition of agents such as thickening agents, buffer salts or acid or alkali to adjust the pH, isotonicity adjusting agents or anti-oxidants.

Solutions for inhalation by nebulation may be formulated with an aqueous vehicle with the addition of agents such as acid or alkali, buffer salts, isotonicity adjusting agents or antimicrobials. They may be sterilised by filtration or heating in an autoclave, or presented as a non-sterile product.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose an acacia.

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds and pharmaceutical formulations according to the invention may be used in combination with or include one or more other therapeutic agents, for example selected from anti-inflammatory agents, anticholinergic agents (particularly an $M_1$, $M_2$, $M_1/M_2$ or $M_3$ receptor antagonist), other $\beta_2$-adrenoreceptor agonists, antiinfective agents (e.g. antibiotics, antivirals), or antihistamines. The invention thus provides, in a further aspect, a combination comprising a compound of formula (I) or a pharmaceutically acceptable salt, solvate or physiologically functional derivative thereof together with one or more other therapeutically active agents, for example selected from an anti-inflammatory agent (for example a corticosteroid or an NSAID), an anticholinergic agent, another $\beta_2$-adrenoreceptor agonist, an antiinfective agent (e.g. an antibiotic or an antiviral), or an antihistamine. Preferred are combinations comprising a compound of formula (I) or a pharmaceutically acceptable salt, solvate or physiologically functional derivative thereof together with a corticosteroid, and/or an anticholinergic, and/or a PDE-4 inhibitor. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, $6\alpha,9\alpha$-difluoro-$17\alpha$-[(2-furanylcarbonyl)oxy]-$11\beta$-hydroxy-$16\alpha$-methyl-3-oxo-androsta-1,4-diene-$17\beta$-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists) or inhibitors of cytokine synthesis. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Of particular interest is use of the compound of formula (I) or (Ia) in combination with a phosphodiesterase 4 (PDE4) inhibitor or a mixed PDE3/PDE4 inhibitor. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4.

A method for determining $IC_{50}$s ratios is set out in U.S. Pat. No. 5,998,428 which is incorporated herein in full by reference as though set out herein. See also PCT application WO 00/51599 for an another description of said assay.

The preferred PDE4 inhibitors of use in this invention will be those compounds which have a salutary therapeutic ratio, i.e., compounds which preferentially inhibit cAMP catalytic activity where the enzyme is in the form that binds rolipram with a low affinity, thereby reducing the side effects which apparently are linked to inhibiting the form which binds rolipram with a high affinity. Another way to state this is that the preferred compounds will have an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity.

A further refinement of this standard is that of one wherein the PDE4 inhibitor has an $IC_{50}$ ratio of about 0.1 or greater; said ratio is the ratio of the $IC_{50}$ value for competing with the binding of 1 nM of [$^3$H]R-rolipram to a form of PDE4 which binds rolipram with a high affinity over the $IC_{50}$ value for inhibiting the PDE4 catalytic activity of a form which binds rolipram with a low affinity using 1 μM[$^3$H]-cAMP as the substrate.

Most preferred are those PDE4 inhibitors which have an $IC_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl) cyclohexan-1-one and cis-[4-cyano-4-(3-cyclopropylmethoxy-4-difluoromethoxyphenyl) cyclohexan-1-ol]; these are examples of compounds which bind preferentially to the low affinity binding site and which have an $IC_{50}$ ratio of 0.1 or greater.

Other compounds of interest include:

Compounds set out in U.S. Pat. No. 5,552,438 issued 03 Sep., 1996; this patent and the compounds it discloses are incorporated herein in full by reference. The compound of particular interest, which is disclosed in U.S. Pat. No. 5,552,438, is cis-4-cyano-4-[3-(cyclopentyloxy)-4-methoxyphenyl]cydohexane-1-carboxylic acid (also known as cilomalast) and its salts, esters, pro-drugs or physical forms; AWD-12-281 from elbion (Hofgen, N. et al. 15th EFMC Int Symp Med Chem (Sept 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (Sept 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Other possible PDE-4 and mixed PDE3/PDE4 inhibitors include those listed in WO01/13953, the disclosure of which is hereby incorporated by reference.

Suitable anticholinergic agents are those compounds that act as antagonists at the muscarinic receptor, in particular those compounds which are antagonists of the $M_1$ and $M_2$ receptors. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to wit:

Atropine—CAS-51-55-8 or CAS-51-48-1 (anhydrous form), atropine sulfate—CAS-5908-99-6; atropine oxide—CAS-4438-22-6 or its HCl salt—CAS4574-60-1 and methylatropine nitrate—CAS-52-88-0.

Homatropine—CAS-87-00-3, hydrobromide salt—CAS-51-56-9, methylbromide salt—CAS-8049-9.

Hyoscyamine (d, l)—CAS-101-31-5, hydrobromide salt—CAS-306-03-6 and sulfate salt—CAS-6835-16-1.

Scopolamine—CAS-51-34-3, hydrobromide salt—CAS-6533-68-2, methylbromide salt—CAS-155-41-9.

Preferred anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118, the disclosure of which is hereby incorporated by reference.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, have a core structure, which can be represented by the following formula:

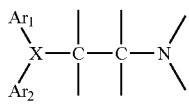

This generalized structure represents three types of antihistamines generally available: ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlorpheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a PDE4 inhibitor.

Examples of preferred anti-histamines include methapyrilene and loratadine.

The invention thus provides, in a further aspect, a combination comprising a compound of formula (I) or (Ia) or a pharmaceutically acceptable salt, solvate or physiologically functional derivative thereof together with a PDE4 inhibitor. Preferably, the invention provides a combination comprising a compound of formula (Ia) or a pharmaceutically acceptable salt, solvate or physiologically functional derivative thereof together with a preferred PDE4 inhibitor as described hereinabove, e.g. cis-4-cyano-4-[3-(cyclopentyloxy)-4-methoxyphenyl]cyclohexane-1-carboxylic acid.

The invention thus provides, in a further aspect, a combination comprising a compound of formula (I) or (Ia) or a pharmaceutically acceptable salt, solvate or physiologically functional derivative thereof together with a corticosteroid. Preferably, the invention provides a combination comprising a compound of formula (Ia) or a pharmaceutically acceptable salt, solvate or physiologically functional derivative thereof together with a preferred corticosteroid as described hereinabove, e.g. fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

The invention thus provides, in a further aspect, a combination comprising a compound of formula (I) or (Ia) or a pharmaceutically acceptable salt, solvate or physiologically functional derivative thereof together with an anticholinergic. Preferably, the invention provides a combination comprising a compound of formula (Ia) or a pharmaceutically acceptable salt, solvate or physiologically functional derivative thereof together with a preferred anticholinergic as described hereinabove, e.g. ipratropium, oxitropium or tiotropium The invention thus provides, in a further aspect, a combination comprising a compound of formula (I) or (Ia) or a pharmaceutically acceptable salt, solvate or physiologically functional derivative thereof together with an antihistamine. Preferably, the invention provides a combination comprising a compound of formula (Ia) or a pharmaceutically acceptable salt, solvate or physiologically functional derivative thereof together with a preferred antihistamine as described hereinabove.

The invention thus provides, in a further aspect, a combination comprising a compound of formula (I) or (Ia) or a pharmaceutically acceptable salt, solvate or physiologically functional derivative thereof together with a PDE4 inhibitor and a corticosteroid. Preferably, the invention provides a combination comprising a compound of formula (Ia) or a pharmaceutically acceptable salt, solvate or physiologically functional derivative thereof together with a preferred antihistamine and a preferred corticosteroid as described hereinabove.

The invention thus provides, in a further aspect, a combination comprising a compound of formula (I) or (Ia) or a pharmaceutically acceptable salt, solvate or physiologically functional derivative thereof together with an anticholinergic and a PDE-4 inhibitor. Preferably, the invention provides a combination comprising a compound of formula (Ia) or a pharmaceutically acceptable salt, solvate or physiologically functional derivative thereof together with a preferred PDE4 inhibitor and a preferred anticholinergic as described hereinabove.

The combinations referred to above may conveniently be presented for use in the form of a pharmaceutical formulation and thus pharmaceutical formulations comprising a combination as defined above together with a physiologically acceptable diluent or carrier represent a further aspect of the invention.

The individual compounds of such combinations may be administered either sequentially or simultaneously in separate or combined pharmaceutical formulations. Appropriate doses of known therapeutic agents will be readily appreciated by those skilled in the art.

According to a further aspect of the invention, there is provided a process for preparing a compound of formula (I) or (Ia) or a salt, solvate, or physiologically functional derivative thereof which comprises a process as defined below followed by the following steps in any order:

(i) optional removal of any protecting groups;

(ii) optional separation of an enantiomer from a mixture of enantiomers;

(iii) optional conversion of one compound of formula (I) to a different compound of formula (I) eg. conversion of a compound wherein $R^1$ is $SR^6$ to a compound wherein $R^1$ is $SOR^6$ or $SO_2R^6$, or conversion of a compound wherein $R^1$ is $SOR^6$ to a compound wherein $R^1$ is $SO_2R^6$;

(iv) optional conversion of a compound wherein $R^6$ represents cycloalkenyl to a compound wherein $R^6$ represents cycloalkyl, eg. by hydrogenation;

(v) optional conversion of the product to a corresponding salt, solvate, or physiologically functional derivative thereof.

In one general process (a), a compound of formula (I) or (Ia), may be obtained by deprotection of a protected intermediate, for example of formula (II):

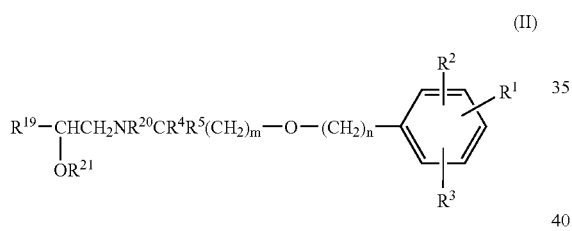

(II)

or a salt or solvate thereof, wherein $R^1$, $R^2$, $R^3$, $R^4$, $R^5$, m, and n are as defined for the compound of formula (I) or (Ia), $R^{19}$ represents an optionally protected form of Ar; and $R^{20}$ and $R^{21}$ are each independently either hydrogen or a protecting group, provided that the compound of formula (II) contains at least one protecting group.

Optionally protected forms of the preferred groups Ar may be selected from:

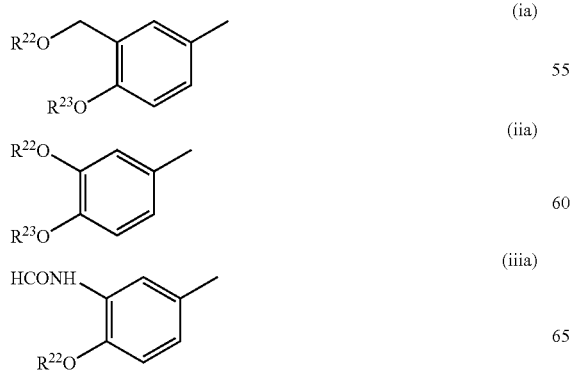

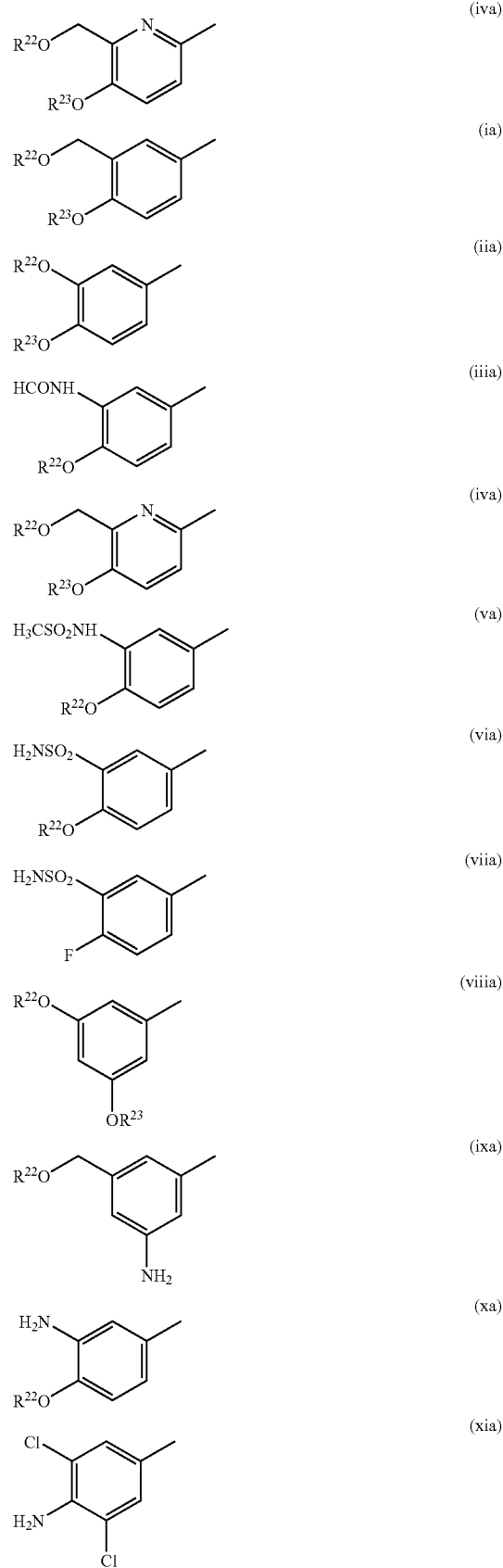

-continued

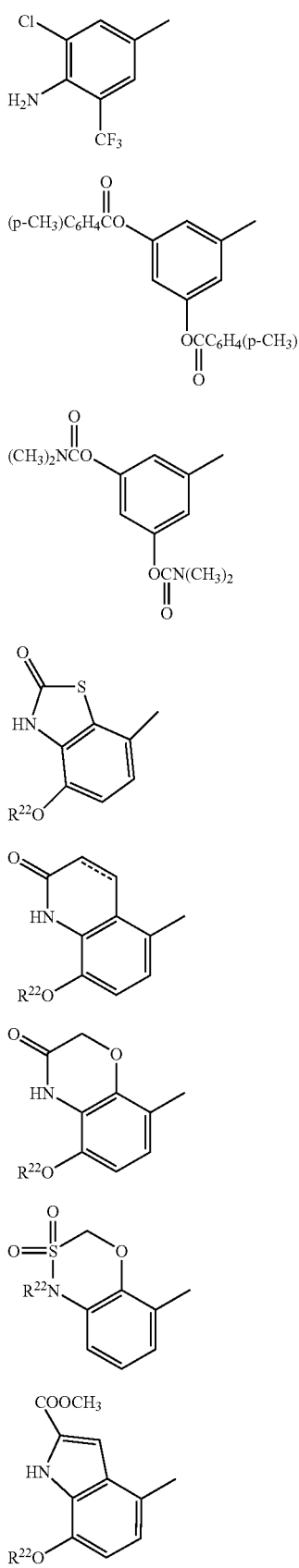

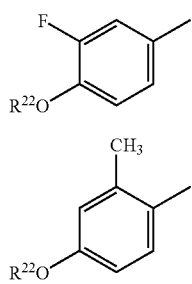

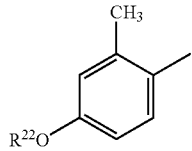

wherein $R^{22}$ and $R^{23}$ are each independently either hydrogen or a protecting group provided that at least one of $R^{22}$ and $R^{23}$ is a protecting group, and the dotted line in (xvia) and (xixa) denotes an optional double bond.

It will be appreciated that to obtain a compound of formula (Ia) in this and the other processes described herein, $R^{19}$ represents the structure (ia) above.

Suitable protecting groups may be any conventional protecting group such as those described in "Protective Groups in Organic Synthesis" by Theodora W Greene and Peter G M Wuts, 3rd edition (John Wiley & Sons, 1999). Examples of suitable hydroxyl protecting groups represented by $R^{22}$ and $R^{23}$ are esters such as acetate ester, aralkyl groups such as benzyl, diphenylmethyl, or triphenylmethyl, and tetrahydropyranyl. Examples of suitable amino protecting groups represented by $R^{20}$ include benzyl, α-methylbenzyl, diphenylmethyl, triphenylmethyl, benzyloxycarbonyl, tert-butoxycarbonyl, and acyl groups such as trichloroacetyl or trifluoroacetyl.

As will be appreciated by the person skilled in the art, use of such protecting groups may include orthogonal protection of groups in the compounds of formula (II) to facilitate the selective removal of one group in the presence of another, thus enabling selective functionalisation of a single amino or hydroxyl function. For example, the —CH(OH) group may be orthogonally protected as —CHOR$^{21}$ using, for example, a trialkylsilyl group such as triethylsilyl. A person skilled in the art will also appreciate other orthogonal protection strategies, available by conventional means as described in Theodora W Greene (see above).

The deprotection to yield a compound of formula (I) or (Ia) may be effected using conventional techniques. Thus, for example, when $R^{22}$, $R^{23}$, and/or $R^{20}$ is an aralkyl group, this may be cleaved by hydrogenolysis in the presence of a metal catalyst (e.g. palladium on charcoal).

When $R^{23}$ and/or $R^{24}$ is tetrahydropyranyl this may be cleaved by hydrolysis under acidic conditions. Acyl groups represented by $R^{20}$ may be removed by hydrolysis, for example with a base such as sodium hydroxide, or a group such as trichloroethoxycarbonyl may be removed by reduction with, for example, zinc and acetic acid. Other deprotection methods may be found in Theodora W Greene (see above).

In a particular embodiment of process (a), when Ar represents a group of structure (i), eg. as in formula (Ia), $R^{22}$ and $R^{23}$ may together represent a protecting group as in the compound of formula (III).

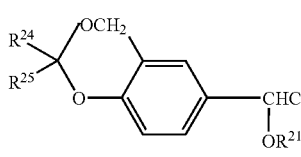

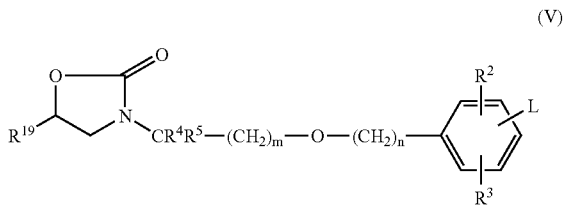

or a salt or solvate thereof, wherein $R^1$, $R^2$, $R^3$, $R^4$, $R^5$, $R^{20}$, $R^{21}$, m, and n are as defined for the compound of formula (I) $R^{24}$ and $R^{25}$ are independently selected from hydrogen, $C_{1-6}$alkyl, or aryl or $R^{24}$ and $R^{25}$ together form a $C_{3-7}$ alkyl group. In a preferred aspect, both $R^{24}$ and $R^{25}$ are methyl.

A compound of formula (III) may be converted to a compound of formula (I) by hydrolysis with dilute aqueous acid, for example acetic acid or hydrochloric acid in a suitable solvent or by transketalisation in an alcohol, for example ethanol, in the presence of a catalyst such as an acid (for example, toluenesulphonic acid) or a salt (such as pyridinium tosylate) at normal or elevated temperature.

It will be appreciated that the protecting groups $R^{22}$, $R^{23}$, $R^{20}$ and $R^{21}$ (including the cyclised protecting group formed by $R^{22}$ and $R^{23}$ as depicted in formula (III) may be removed in a single step or sequentially. The precise order in which protecting groups are removed will in part depend upon the nature of said groups and will be readily apparent to the skilled worker. Preferably, when $R^{22}$ and $R^{23}$ together form a protecting group as in formula (III) this protecting group is removed together with any protecting group on the CH(OH) moiety, followed by removal of $R^{20}$.

Compounds of formulae (II) and (III) wherein $R^{20}$ and $R^{21}$ represent hydrogen may be prepared from the corresponding compound of formula (IV):

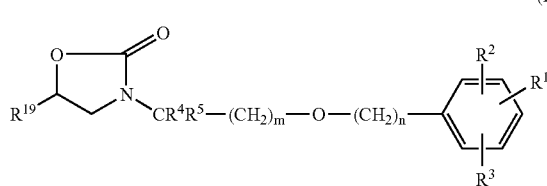

or a salt or solvate thereof, wherein $R^1$, $R^2$, $R^3$, $R^4$, $R^5$, $R^{19}$, m, and n are as defined for the compound of formula (II) or (III).

The conversion of a compound of formula (IV) to a compound of formula (II) or (III) may be effected by treatment with a base, for example a non-aqueous base, such as potassium trimethylsilanolate, or an aqueous base such as aqueous sodium hydroxide, in a suitable solvent such as tetrahydrofuran.

Compounds of formula (IV) wherein $R^1$ represents a group $SR^6$ may be prepared from the corresponding compound of formula (V):

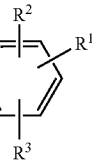

wherein $R^2$, $R^3$, $R^4$, $R^5$, $R^{19}$, m, and n are as defined for formula (II) and L is a leaving group, for example a halo group, (preferably iodo);

by reaction with a compound $R^6SH$ in the presence of 1,1 bis-(diphenyl phosphine) ferrocene, tris(dibenzylidene acetone) di-palladium, N-methylpyrrolidinone and an organic base such as triethylamine. The sulfide product initially obtained from this reaction may if desired be oxidised to give the corresponding compound of formula (IV) wherein $R^1$ represents a group $SOR^6$. Oxidation may be carried out using conventional oxidising agents, for example sodium periodate, in a suitable solvent, for example an alcohol such as ethanol, or a peracid, for example, metachloroperbenzoic acid in a suitable solvent such as dichloromethane, or hydrogen peroxide in a suitable solvent such as acetic acid.

When $R^1$ represents $SOR^6$ the product may initially be obtained as a mixture of diastereoisomers. These may be separated by conventional methods, for example using chiral chromatography, such as chiral HPLC. Alternatively the sulphoxides can be prepared selectively in one of the diastereomeric forms by the use of a chiral oxidising agent.

A compound of formula (IV) wherein $R^1$ represents $SO_2R^6$ may be prepared by oxidation of a corresponding compound of formula (IV) wherein $R^1$ represents $SOR^6$ or $SR^6$ by reaction with a peracid, for example metachloroperbenzoic acid. When a sulfide (ie $R^1$ represents $SR^6$) is employed as the starting material, the peracid should be used in excess, to ensure complete oxidation. A sulphoxide starting material may conveniently be employed as a mixture of diastereoisomers.

It will be appreciated by those skilled in the art that whilst it is possible to react a compound of formula (V) with a compound $R^6SH$ wherein $R^6$ represents either a cycloalkyl or cycloalkenyl group, any subsequent oxidation step effected on a compound (IV) wherein $R^6$ represents a cycloalkenyl group, will also result in oxidation of said cycloalkenyl group. However, compounds (IV) wherein $R^1$ represents $SOR^6$ or $SO_2R^6$ wherein $R^6$ is a cycloalkenyl group may be prepared by the methodology described in process (b) hereinbelow.

Compounds of formula (IV) may also be prepared by methods analogous to processes (c) and (d) below, for example by reacting a compound of formula (VI) with a compound of formula (XVII) as defined hereinbelow.

A compound of formula (V) may be prepared by coupling a compound of formula (VI):

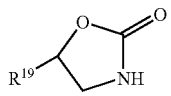  (VI)

or a salt or solvate thereof, wherein $R^{19}$ is as defined for the compound of formula (V) with a compound of formula (VII):

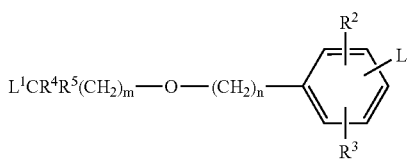  (VII)

wherein $R^4$, $R^5$, L, m and n are as defined for the compound of formula (V) and $L^1$ is a leaving group, for example a halo group (typically bromo or iodo) or a sulfonate such as an alkyl sulfonate (typically, methanesulfonate), an arylsulfonate (typically, toluenesulfonate), or a haloalkyl sulfonate (typically, trifluoromethanesulfonate).

The coupling of a compound of formula (VI) with a compound of formula (VII) may be effected in the presence of a base, such as a metal hydride, for example sodium hydride, or an inorganic base such as cesium carbonate, in an aprotic solvent, for example N,N-dimethylformamide or tetrahydrofuran.

Compounds of formula (VI) may be prepared for example as described in WO 02/066422.

Compounds of formula (VII) may be prepared from a corresponding dihaloalkane of formula (VIII):

  (VIII)

wherein $R^4$, $R^5$ and m are as defined for compounds of formula (I) and each $L^1$ represents a halo, typically bromo;

by reaction with an alcohol of formula (IX):

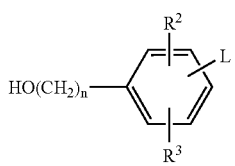  (IX)

wherein $R^2$, $R^3$, L and n are as defined for compounds of formula (VII).

It will be appreciated that when the group L in compounds of formula (VII) represents bromo, this may, if desired, be exchanged for an iodo substituent by reaction with iodine in the presence of an alkyl lithium, such as n-butyl lithium, in a solvent such as tetrahydrofuran.

The coupling of compounds (VIII) and (IX) may be effected in the presence of an inorganic base, such as aqueous sodium hydroxide, under phase transfer conditions in the presence of an ammonium salt such as tetraalkylammonium bromide.

Compounds of formula (VIII) and (IX) are known or may be prepared by standard methods.

Compounds of formula (I), (II) or (III) may also be prepared as described in processes (b)-(e) below.

Thus in a further process (b) a compound of formula (I), (II) or (III) wherein $R^1$ represents a group $SO_2R^6$ and $R^6$ represents a cycloalkenyl group may be prepared from a compound of formula (X):

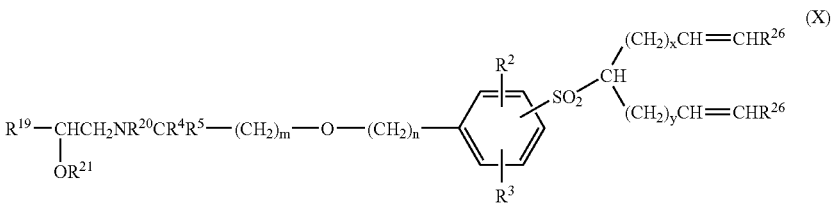  (X)

wherein $R^2$, $R^3$, $R^4$, $R^5$, m and n are as defined for formula (I), $R^{19}$ is an optionally protected form of Ar, $R^{20}$ and $R^{21}$ each independently represent hydrogen or a protecting group, each $R^{26}$ independently represents hydrogen or $C_{1-4}$alkyl, and x and y each represent 0, 1 or 2;

by effecting ring closure to form a cycloalkenyl group.

Ring closure may be effected by olefin metathesis chemistry. In this method a compound of formula (X) is reacted with a ruthenium catalyst (Grubbs catalyst) such as benzylidene-bis(tricyclohexylphosphine)-dichlororuthenium, or a molybdenum (Schrock) catalyst, to effect formation of the desired cycloalkene moiety, with concomitant generation of ethylene or a substituted ethylene, preferably as a gas. $R^{26}$ is preferably a small moiety, eg. hydrogen or methyl, most preferably hydrogen. Preferably a ruthenium catalyst is employed. The catalyst may if desired be polymer-supported. A review of metathesis chemistry and catalysts is given by S J Connon and S Blechert, Angew. Chem. Int. Ed. 2003, 42, 1900.

A compound of formula (X) may be prepared by reacting a compound of formula (XI):

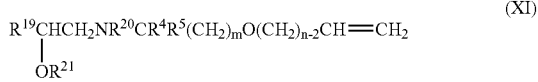  (XI)

wherein $R^4$, $R^5$, $R^{19}$, $R^{20}$, $R^{21}$, m and n are as hereinbefore defined for compounds of formula (X), with a compound of formula (XII):

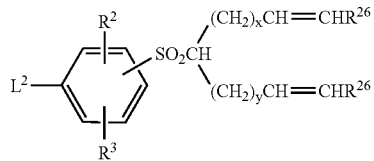

(XII)

wherein $R^2$, $R^3$, $R^{26}$, x and y are as defined for formula (X) and $L^2$ is halo eg. bromo.

In this method, a compound of formula (XI) is initially reacted with a sterically hindered borane compound eg. a cyclic borane derivative such as 9-borabicyclo[3.3.1]nonane, thexylborane, catecholborane or disiamylborane, and followed by coupling with the compound (XII) in the presence of a catalyst such as palladium acetate, $PdCl_2$, $Pd(PPh_3)_4$, or $Pd_2(dba)_3$; and a phosphine such as triphenylphosphine, (di-tert-butylphosphino)biphenyl, tricyclohexylphosphine, tri-isopropylphosphine, tricyclopentylphosphine, or tri-tert-butylphosphine; and a base such as aqueous potassium or sodium phosphate, potassium or sodium carbonate, or sodium acetate.

A compound of formula (XI) may be prepared for example by reacting a compound of formula (XIII):

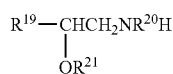

(XIII)

wherein $R^{19}$, $R^{29}$ and $R^{21}$ are as hereinbefore defined;

with a compound of formula (XIV):

(XIV)

wherein $L^1$, $R^4$, $R^5$, m and n are as defined for formula (VI).

Compounds of formula (XIII) are known in the art (for example EP-A 0947498 or WO 02/070490) or may be readily prepared by a person skilled in the art.

Further details concerning preparation of compounds (XIII) wherein $R^{19}$ is a group (v) can be found in DE3524990; concerning the preparation of compounds (XIII) wherein $R^{19}$ is a group (ii), (viii), and (xvi) in EP-A-162576; concerning the preparation of compounds (XIII) wherein $R^{19}$ is a group (iv) in EP-A-220054; concerning the preparation of compounds (XIII) wherein $R^{19}$ is a group (xi) in GB2165542 and concerning the preparation of compounds (XIII) wherein $R^{19}$ is a group (c) in GB2230523.

A compound of formula (XIV) may be prepared by standard methods, e.g. from the corresponding dihaloalkane and hydroxyalkene by conventional chemistry, typically in the presence of an inorganic base, such as aqueous sodium hydroxide, under phase transfer conditions in the presence of an ammonium salt such as tetraalkylammonium bromide.

A compound of formula (XII) may be prepared by reacting a compound of formula (XV):

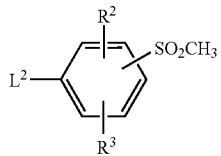

(XV)

with a base, such a lithium bis(trimethylsilyl)amide in a solvent such as tetrahydrofuran, followed by reaction with an alkenyl halide of formula:

$L^2(CH_2)_xCH\!=\!CHR^{26}$ or, where x and y in formula (XII) each have different values by stepwise reaction with each of $L^2(CH_2)_xCH\!=\!CHR^{26}$ and $L^2(CH_2)_yCH\!=\!CHR^{26}$.

Alternatively, where x and/or y represent zero, the moiety $-O_2CH(CH\!=\!CHR^{26})_2$ or $-SO_2CH_2CH\!=\!CHR^{26}$ may be coupled directly with the aromatic ring by conventional methods.

Compounds of formula (XV) may be prepared by standard methods eg. as described in Tet. Letts. 1994, 35, 9063.

It will be appreciated that a compound of formula (IV) wherein $R^1$ represents $-SO_2R^6$ and $R^6$ represents cycloalkenyl may also be prepared by the method of process (b), using a compound of formula (XVI):

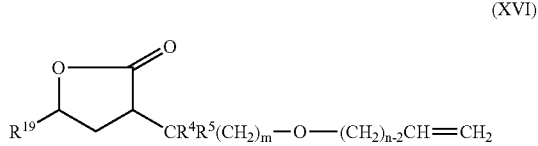

(XVI)

wherein $R^4$, $R^5$, $R^{19}$, m and n are as defined for compounds of formula (II), which in turn may be prepared by reacting a compound of formula (VI) with a compound of formula (XIV) in an analogous manner to the reaction of a compound (XIII) with a compound (XIV).

It will further be appreciated that the step of forming the cycloalkenyl group $R^6$, may be carried out at any convenient stage of the reaction. However, in order to retain the cycloalkenyl moiety, this step should be carried out after any stages involving hydrogenation, hydroboration or oxidation reactions.

In a further process (c), a compound of formula (I), (II) or (III) may be obtained by alkylation of an amine of formula (XIII):

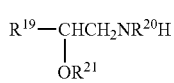

(XIII)

wherein $R^{19}$, represents an optionally protected form of Ar and $R^{20}$ and $R^{21}$ are each independently either hydrogen or a protecting group, eg. as defined hereinabove for formula (II);

with a compound of formula (XVII):

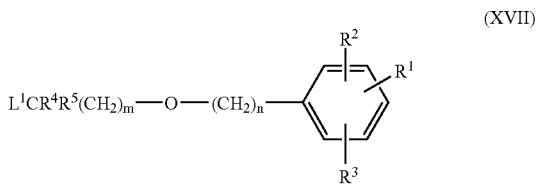
(XVII)

wherein $R^1$, $R^2$, $R^3$, $R^4$, $R^5$, m, and n are as defined for the compound of formula (I) and $L^1$ is a leaving group such as halo (typically bromo) or a sulfonate eg a haloalkyl sulfonate (typically trifluoromethane sulfonate); followed by removal of any protecting groups present by conventional methods as described above for the deprotection of compounds of formula (II).

The reaction of a compound of formula (XIII) with a compound of formula (XVII) is optionally effected in the presence of an organic base such as a trialkylamine, for example, diisopropylethylamine, and in a suitable solvent for example dimethyl formamide.

A compound of formula (XVII) may be prepared by reacting an olefin of formula (XIV):

(XIV)

wherein $L^1$, $R^4$, $R^5$, m and n are as defined for formula (XI), with a compound of formula (XVIII).

(XVIII)

wherein $R^1$, $R^2$ and $R^3$ are as defined hereinabove for formula (I) and $L^2$ is a halo, eg. bromo;

in an analogous manner to the reaction of a compound (XI) with a compound (XII) as described hereinabove in process (b);

or by reacting a compound (XIV) with a compound of formula (XII) followed by a metathesis reaction as described in process (b) hereinabove.

Compounds of formula (XVIII) wherein $R^1$ is $SR^6$, $SOR^6$, or $SO_2R^6$ and $R^6$ represents a cycloalkyl group are commercially available or may be prepared by methods well known to the person skilled in the art.

A compound of formula (XVII) may also be prepared by reduction of a compound of formula (XX) as defined hereinafter.

In a yet further process (d) a compound of formula (I), (II) or (III) may be obtained by reduction of a compound of formula (XIX):

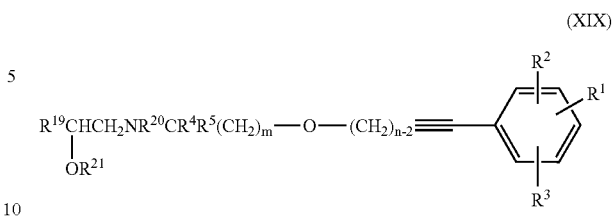
(XIX)

wherein $R^1$, $R^2$, $R^3$, $R^4$, $R^5$, m and n are as defined for formula (I), $R^{19}$ represents an optionally protected form of Ar and $R^{20}$ and $R^{21}$ are each independently hydrogen or a protecting group as defined above.

The reduction may be effected by any suitable method such as hydrogenation in the presence of a catalyst, for example, palladium/charcoal or platinum oxide.

It will be understood by those skilled in the art that if $R^1$ contains a cycloalkenyl moiety this will also be hydrogenated to the corresponding cycloalkyl moeity. Hence this method is not appropriate when it is desired to obtained a product wherein $R^1$ contains a cycloalkenyl group.

It will be appreciated that where $R^{19}$ represents Ar and $R^{20}$ and $R^{21}$ each represent hydrogen, the reduction will yield a compound of formula (I), but where one or more of $R^{19}$, $R^{20}$ and $R^{21}$ contains or represents a protecting group then reduction will yield a compound of formula (II) or (III), which may then be deprotected to give a compound of formula (I).

A compound of formula (XIX) may be prepared by reacting a compound of formula (XIII):

$$R^{19}\!\!-\!\!\underset{\underset{OR^{21}}{|}}{C}HCH_2NR^{20}H \quad (XIII)$$

as hereinbefore defined with a compound of formula (XX):

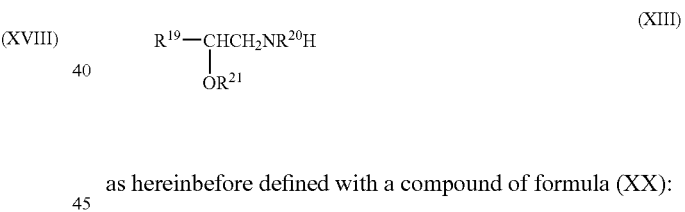
(XX)

wherein $R^1$, $R^2$, $R^3$, $R^4$, $R^5$, m, and n are as defined for the compound of formula (I) and $L^1$ is as defined for the compound of formula (VII) hereinabove.

The reaction of a compound of formula (XIII) with a compound of formula (XX) is optionally effected in the presence of an organic base such as a trialkylamine, for example, diisopropylethylamine, and in a suitable solvent for example N,N-dimethylformamide.

A compound of formula (XX) may be prepared by coupling a compound of formula (XVIII):

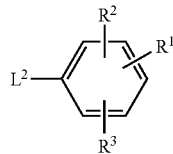

(XVIII)

as hereinbefore defined, with a compound of formula (XXI):

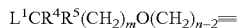

(XXI)

wherein $L^1$, $R^4$, $R^5$, m and n are as defined above for compounds of formula (XV):

Alternatively, a compound of formula (XIX) may be prepared by reacting a compound of formula (XVIII) as hereinbefore defined with a compound of formula (XXII):

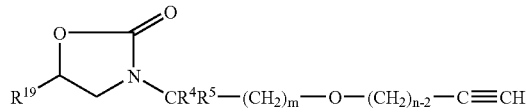

(XXII)

or a salt or solvate thereof, wherein $R^4$, $R^5$, m, n and $R^{19}$ are as defined for the compound of formula (XIX), followed by opening of the oxazolidinone ring as described in process (a).

The coupling of a compound of formula (XVIII) with a compound of formula (XXI) or (XXII) is conveniently effected in the presence of a catalyst system such as bis(triphenylphosphine) palladium dichloride and in the presence of a copper catalyst eg. cuprous iodide, with an organic base such as a trialkylamine, for example, triethylamine, in a suitable solvent, for example acetonitrile or dimethylformamide.

A compound of formula (XXII) may be prepared by coupling a compound of formula (VI) as hereinbefore defined with a compound of formula (XXI) as hereinbefore defined.

The coupling of a compound of formula (VI) with a compound of formula (XXI) may be effected in the presence of a base, such as a metal hydride, for example sodium hydride, or an inorganic base such as caesium carbonate, in an aprotic solvent, for example dimethylformamide.

Compounds of formula (XXI) may be prepared from the corresponding dihaloalkane and hydroxyalkyne by conventional chemistry, typically in the presence of an inorganic base, such as aqueous sodium hydroxide, under phase transfer conditions in the presence of an ammonium salt such as tetraalkylammonium bromide.

In a further process (e) a compound of formula (I), (II) or (III) may be prepared by reacting a compound of formula (XXIII):

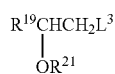

(XXIII)

wherein $R^{19}$ is as hereinbefore defined and $L^3$ is a leaving group as defined above for $L^1$ or $L^2$;

or a compound of formula (XXIV):

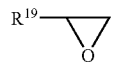

(XXIV)

wherein $R^{19}$ is as hereinbefore defined with an amine of formula (XXV):

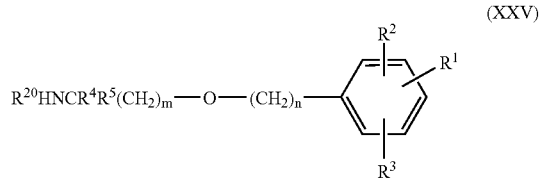

(XXV)

followed by removal of any protecting groups present by conventional methods as described above for the deprotection of compounds of formula (II).

The reaction may be effected using conventional conditions for such displacement reactions.

Compounds of formula (XXIII) and (XXIV) may be prepared by methods known in the art.

A compound of formula (XXV) may be prepared by reacting a compound of formula (XVII) with an amine $R^{20}NH_2$.

In a further process (f) a compound of formula (I), (II) or (III) may be prepared by removal of a chiral auxiliary from a compound of formula (IIa):

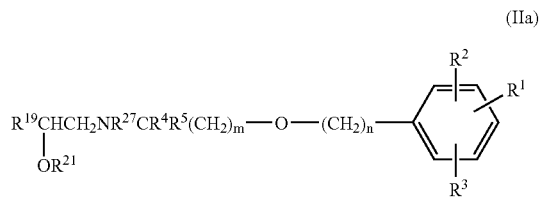

(IIa)

wherein $R^1$-$R^5$, m and n are as defined for formula (I), $R^{19}$ represents an optionally protected form of Ar, $R^{21}$ represent hydrogen or a protecting group and $R^{27}$ represents a chiral auxiliary.

A "chiral auxiliary" is a moiety that is introduced into a molecule to influence the stereochemistry of the product formed, and is removed in whole or part at a later time. A chiral auxiliary may simultaneously function as a protecting group.

Many chiral auxiliaries are commercially available, and persons skilled in the art would choose one based on the properties desired i.e. the absolute stereochemistry desired and compatibility with the processes being used. Chiral auxiliaries suitable for use in this process include but are not limited to the S-isomer and/or the R-isomer of phenyl glycinol and substituted derivatives thereof.

The chiral auxiliary is preferably a moiety of the formula:

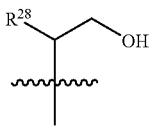

or a single enantiomer thereof, wherein $R^{28}$ represents $C_{1-6}$alkyl or optionally substituted phenyl or benzyl wherein the optional substitution is one or more independently selected from $C_{1-6}$alkyl, halogen, hydroxy, $C_{1-6}$alkoxy or nitro e.g. para-hydroxyphenyl.

More preferably the chiral auxiliary is a moiety:

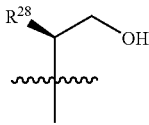

wherein $R^{28}$ is as defined above. Alternatively it may be a moiety of formula:

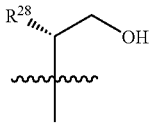

wherein $R^{28}$ is as defined above.

Preferably $R^{28}$ represents phenyl optionally substituted as described above. Most preferably $R^{28}$ represents unsubstituted phenyl.

The chiral auxiliary in this process may typically be removed by hydrogenolysis using for example a palladium on carbon catalyst or preferably using palladium hydroxide (Pearlman's catalyst). Advantageously when Pearlman's catalyst is used the removal of the chiral auxiliary is most efficient. This method of removal is especially suitable where $R^{18}$ is phenyl or a substituted phenyl. Alternatively the nitrogen, to which the auxiliary is attached, may be derivatised under oxidising conditions to form the N-oxide before elimination by heating to give a secondary amine.

A compound of formula (IIa) may be prepared by methods analogous to those described above, for example process (c).

A detailed description of a proces analogous to Route (e) may be found in published International Application Number WO/0/196278.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly. Thus for example, as previously indicated, where it is desired that $R^6$ in the final product represents a cycloalkenyl moiety, this should be introduced after any hydrogenation, hydroboration or oxidation reactions.

The enantiomeric compounds of the invention may be obtained (i) by separation of the components of the corresponding racemic mixture, for example, by means of a chiral chromatography column, enzymic resolution methods, or preparing and separating suitable diastereoisomers, (ii) by direct synthesis from the appropriate chiral intermediates by the methods described above, or (iii) by enantioselective oxidation of the sulphur atom.

Optional conversions of a compound of formula (I) or (Ia) to a corresponding salt may conveniently be effected by reaction with the appropriate acid or base. Optional conversion of a compound of formula (I) or (Ia) to a corresponding solvate or physiologically functional derivative may be effected by methods known to those skilled in the art.

In a preferred embodiment, in any of the processes described above, $R^{19}$ represents a group (ia):

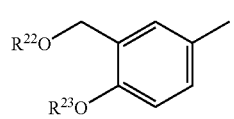

(ia)

such that the final product is a compound of formula (Ia).

According to a further aspect, the present invention provides a novel intermediate for the preparation of compounds of formula (I) and/or (Ia) for example:

a compound of formula (II) (III) (IV) (X) or (XIX) as defined above, or as named in the specific examples hereinbelow, or an optical isomer, a salt, or a protected derivative thereof.

Figure 1:
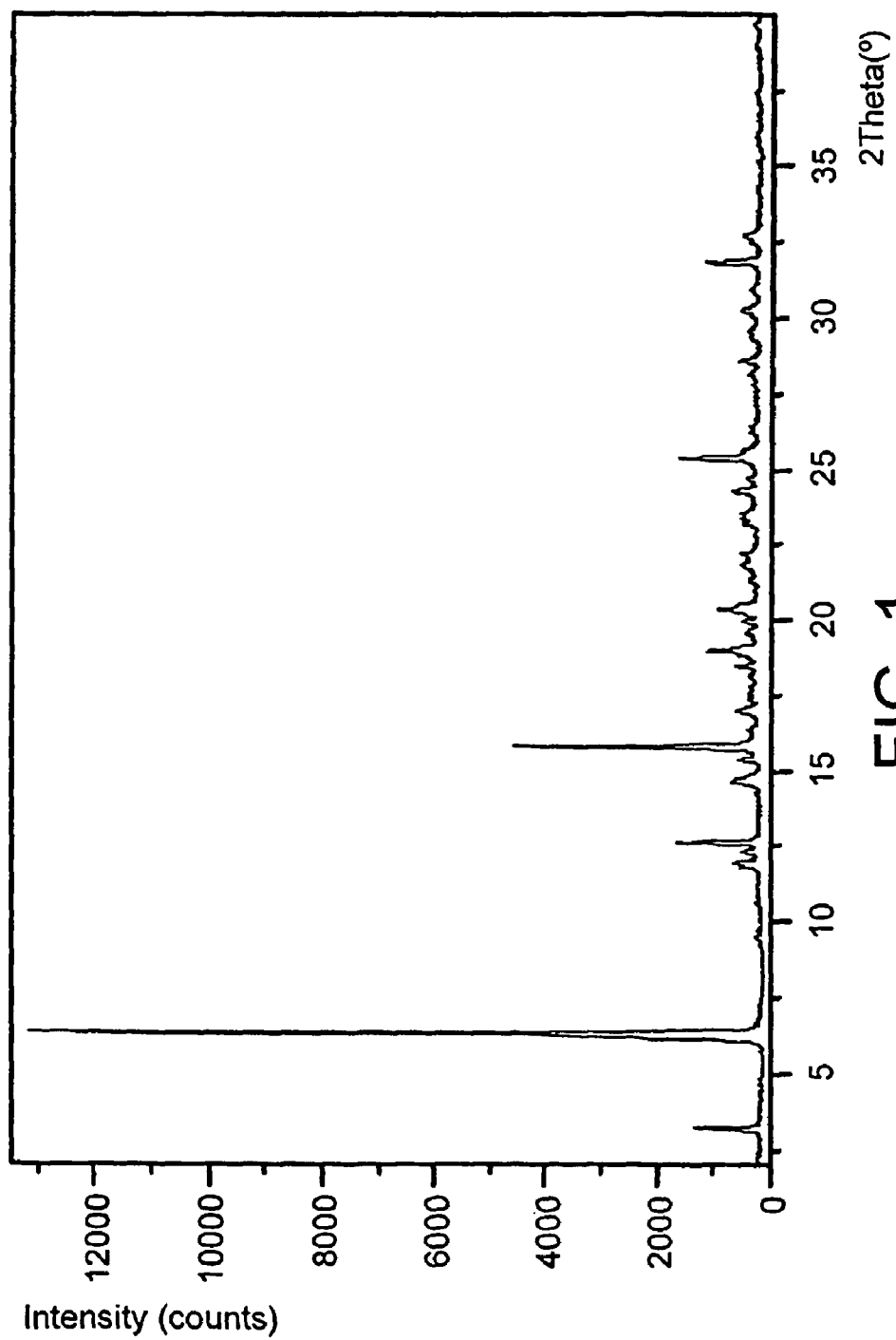
FIG. 1 shows an X-ray powder diffraction pattern of 4-{(1R)-2-[(6-{4-[3-(cyclopentylsulfonyl)phenyl]butoxy}hexyl)amino]-1-hydroxyethyl}-2-(hydroxymethyl)phenol 4-chlorobenzene sulfonate.

For a better understanding of the invention, the following Examples are given by way of illustration.

SYNTHETIC EXAMPLES

Throughout the examples, the following abbreviations are used:
LC: Liquid Chromatography
LCMS: Liquid Chromatography Mass Spectrometry.
RT: retention time
THF: tetrahydofuran
DMF: N,N-dimethylformamide
MeCN: acetonitrile
$PPh_3$: tripherylphosphine AcOH: glacial acetic acid
EtOAc: ethyl acetate
PE: petroleum ether
EtOH: ethanol
bp: boiling point
ca: circa
h: hour(s)
min: minute(s)
All temperatures are given in degrees centigrade.
Silica gel refers to Merck silica gel 60 Art number 7734.
Flash silica gel refers to Merck silica gel 60 Art number 9385.
Biotage refers to prepacked silica gel cartridges containing KP-Sil run on flash 12i chromatography module.
SPE Bond Elut are prepacked cartridges used in parallel purifications, normally under vacuum. These are commercially available from Varian.
NMR experiments at 400 MHz (unless specified otherwise).
LCMS was conducted on a Supelcosil LCABZ+PLUS column (3.3 cm×4.6 mm ID) eluting with 0.1% $HCO_2H$ and 0.01 M ammonium acetate in water (solvent A), and 0.05% $HCO_2H$ 5% water in acetonitrile (solvent B), using the following elution gradient 0-0.7 min 0% B, 0.7-4.2 min 100% B, 4.2-5.3 min 100% B, 5.3-5.5 min 0% B at a flow rate of 3 ml/min. The mass spectra were recorded on a Fisons VG Platform spectrometer using electrospray positive and negative mode (ES+ve and ES−ve).

The XRPD analysis shown in the Figures were performed on a Phillips X'pert Pro powder diffractometer, Model PW3040/60, serial number DY1379 using an X'Celerator detector. The method runs from 2 to 40 degrees 2Theta with 0.0167 degree 2Theta step size and a 31.75 seconds collection time at each step.

Example 1

4-{(1R)-2-[(6-{4-[3-(Cyclopentylsulfinyl)phenyl]butoxy}hexyl)amino]-1-hydroxyethyl}-2-(hydroxymethyl)phenol acetate i) 6-Bromohexyl 4-(3-bromophenyl)butyl ether A stirred mixture of 4-3-bromophenyl) butan-1-ol (18 g) (EP 0 995 752A1), 1,6 dibromohexane (48 ml), tetrabutylammonium bromide (1.5 g) and 50% aqueous sodium hydroxide solution (500 ml) was stirred for 2 days at ambient temperature. The mixture was poured into water (1000 ml) and extracted into ethyl acetate. The combined extracts were washed with water, dried ($Na_2SO_4$) and evaporated. The residual oil was purified on the biotage eluting with light petroleum (40-60° C.), and then light petroleum (40-60° C.)-ether (9:1). The appropriate fractions were evaporated to give the title compound (18 g) LCMS RT=4.34 min.

ii) 6-Bromohexyl 4-(3-iodophenyl)butyl ether

A solution of n-butyl lithium in hexane (1.6 M; 50 ml) was added to a stirred solution of 6-bromophenyl 4-(3-bromophenyl)butyl ether (21 g) in dry THF (150 ml) at −85° C. under nitrogen. After 15 min a solution of iodine (19.8 g) in THF (100 ml) was added dropwise over 20 min. The solution was then allowed to warm up to 0° C. and aqueous sodium bisulphite was added. The mixture was poured into water and extracted into ether. The combined extracts were dried ($Na_2SO_4$) and evaporated. The residue was purified by flash silica gel column chromatography (1 kg) eluting with cyclohexane-ether (9:1). The appropriate fractions were evaporated to give the title compound (17 g). LCMS RT=4.41 min.

iii) Di(tert-butyl) 2-(2,2-dimethyl-4H-1,3-benzodioxin-6-yl)-2-oxoethylimidodicarbonate Cesium carbonate (70.4 g) was added to a stirred suspension of 2-bromo-1-(2,2-dimethyl-4H-1,3-benzodioxin-6-yl)ethanone, (Glaxo, DE 3513885, 1985) (61.8 g) and di-t-butyl iminodicarboxylate (47.15 g) in acetonitrile (600 ml) under nitrogen. After vigorous stirring at 21° for 24 h the mixture was diluted with water (ca800 ml) and the product was extracted with diethyl ether (1 litre, then 200 ml). The combined organic layers were washed with brine, dried ($MgSO_4$) and concentrated to ca400 ml. The white crystals were collected by filtration, washed with diethyl ether and dried to give the title compound (24.4 g) δ ($CDCl_3$) 7.78(1H, dd, J 8, 2 Hz), 7.65 (1H, brs), 6.87(1H, d, J=8 Hz), 4.97(2H, s), 4.88(2H, s), 1.56(6H, s) and 1.48 (18H, s). Further concentration of the mother liquors gave additional product (13.8 g). A third crop (7.1 g) was obtained by chromatographing the mother liquors on silica gel, evaporating the appropriate eluate and triturating with diethyl ether.

iv) tert-Butyl 2-[2,2-dimethyl-4H-1,3-benzodioxin-6-yl)-2-oxoethylcarbamate

Trifluoroacetic acid (92 ml) was added to a stirred solution of di(tert-butyl) 2-(2,2-dimethyl-4H-1,3-benzodioxin-6-yl)-2-oxoethylimidodicarbonate, (352.55 g) in dichloromethane (3.6 litres) at 21° and the reaction was stirred for 1.5 h. Aqueous NaOH solution (1.75 litres) was added and after 10 min the phases were separated. The organic layer was washed with water, dried ($MgSO_4$) and evaporated to an oil. This was stored under high vacuum overnight and then triturated with hexane:ether (3:1) to give the crude product (226.61 g). This was purified by recrystallisation from diethyl ether to give the title compound (122.78 g). Further product (61.5 g) was obtained from the mother liquors by evaporation and chromatography on a Biotage using 15% ethyl acetate in hexane. LCMS RT=3.37 min.

v) tert-Butyl (2R)-2-(2,2-dimethyl-4H-1,3-benzodioxin-6-yl)-2-hydroxyethylcarbamate A 2M solution of borane-dimethyl sulphide in THF (28 ml) was added slowly to a 1M solution of (R)-tetrahydro-1-methyl-3,3-diphenyl-1H,3H-pyrrolo[1,2-c][1,3,2]oxazaborole in toluene (56 ml) at 0° under nitrogen. A solution of tert-butyl 2-(2,2-dimethyl-4H-1,3-benzodioxin-6-yl)-2-oxoethylcarbamate, (108.2 g) in THF (1.3 litres) was added slowly keeping the temperature below 5° followed by 2M solution of borane-dimethyl sulphide in THF (252 ml) over 50 min. After 1 h, 2M HCl (170 ml) was added with cooling and the mixture was partitioned between ethyl acetate and water. The organic layer was washed with saturated $NaHCO_3$ solution and brine and dried ($MgSO_4$). The solution was concentrated and the product purified by chromatography on flash silica gel (800 g), eluting successively with hexane:ethyl acetate (4:1 then 3:1) to give the title compound (93.39), LCMS RT=3.31 min.

vi) (5R)-5-(2,2-Dimethyl-4H-1,3-benzodioxin-6-yl)-1,3-oxazolidin-2-one tert-Butyl (2R)-2-(2,2-dimethyl-4H-1,3-benzodioxin-6-yl)-2-hydroxyethylcarbamate, (86.37 g) in DMF (600 ml) was added dropwise to a stirred suspension of sodium hydride (60% oil dispersion, 11.9 g) in DMF (160 ml) with cooling such that the internal temperature remained at 0° under nitrogen. The mixture was stirred at 21° for 2 h. The mixture was recooled to 0° and 2M HCl (134 ml) was added. The mixture was diluted with water and the product was extracted with ethyl acetate twice. The solution was washed with brine twice, dried (MgSO$_4$) and evaporated to give the title compound (63.55 g) LCMS RT=2.66 min.

vii) (5R)-5-(2,2-Dimethyl-4H-1,3-benzodioxin-6-yl)-3-{6-[4-(3-iodophenyl)butoxy]hexyl}-1,3-oxazolidin-2-one Sodium hydride (60% dispersion in oil 1.26 g) was added to a stirred, cooled (ice-bath) solution of (5R)-5-(2,2-dimethyl-4H-1,3-benzodioxin-6-yl)-2-oxazolidinone (5.47 g) in dry DMF (50 ml) under nitrogen and the mixture was stirred for 15 min at 50° C. A solution of 6-bromohexyl 4-(3-iodophenyl)butyl ether (10.7 g) in DMF (30 ml) was then added dropwise over 10 min. The mixture was stirred for 2 h at ambient temperature, then poured into aqueous solution of ammonium chloride and extracted into ethyl acetate. The combined extracts were washed with water, dried (Na$_2$SO$_4$) and evaporated. The residue was purified on biotage (90 g cartridge) eluting with ether-hexane (3:2) to give the title compound (9.8 g). LCMS RT=4.20 min.

viii) (5R)-3-(6-{4-[3-(Cyclopentylthio)phenyl]butoxy}hexyl)-5-(2,2-dimethyl-4H-1,3-benzodioxin-6-yl)-1,3-oxazolidin-2-one A stirred solution of (5R)-5-(2,2-dimethyl-4H-1,3-benzodioxin-6-yl)-3-{6-[4-(3-iodophenyl)butoxy]hexyl}-1,3-oxazolidin-2-one (1.8 g), 1,1 bis(diphenylphosphino) ferrocene (86 mg) and tris(dibenzylideneacetone) di palladium (180 mg) was stirred at room temperature in 1-methyl-2-pyrrolidinone (10 ml) and triethylamine (2 ml) for 10 min under nitrogen. Cyclopentyl mercaptan (0.63 ml) was added and the mixture was heated at 60° C. for 1 h. The mixture was cooled, poured into water and extracted into dichloromethane. The extracts were dried (Na$_2$SO$_4$) and evaporated. The residual oil was purified on a biotage cartridge (90 g) using ether-hexane (3:2) as eluent changing to ether. The appropriate fractions were evaporated to give the title compound (1.07 g).
LCMS RT=4.31 min.

ix) (5R)-3-(6-{4-[3-(Cyclopentylsulfinyl)phenyl]butoxy}hexyl)-5-(2,2-dimethyl-4H-1,3-benzodioxin-6-yl)-1,3-oxazolidin-2-one Sodium periodate (1.5 g) was added to a stirred solution of (5R)-3-(6-{4-[3-(cyclopentylthio)phenyl]butoxy}hexyl)-5-(2,2-dimethyl-4H-1,3-benzodioxin-6-yl)-1,3-oxazolidin-2-one (1.0 g) in ethanol (20 ml) and water (10 ml) at room temperature. After 2 h the solution was concentrated in-vacuo (ca 50% vol), diluted with water and extracted into dichloromethane. The extracts were dried (Na$_2$SO$_4$) and evaporated to dryness. The residual oil was purified on a biotage cartridge (40 g) using ethyl acetate as the eluent. The appropriate fractions were evaporated to give the title compound (0.68 g). LCMS RT=3.66 min x) (1R)-2-[(6-{4-[3-(Cyclopentylsulfinyl)phenyl]butoxy}hexyl)amino]-1-(2,2-dimethyl-4H-1,3-benzodioxin-6-yl)ethanol A stirred mixture of (5R)-3-(6-{4-[3-(cyclopentylsulfinyl)phenyl]butoxy}hexyl)-5-(2,2-dimethyl-4H-1,3-benzodioxin-6-yl)-1,3-oxazolidin-2-one (0.14 g) and potassium trimethyl silanolate (0.45 g) in tetrahydrofuran (10 ml) was heated to reflux for 2 h. The mixture was poured into phoshate buffer solution (pH 5, 50 ml) and extracted into ethyl acetate. The extracts were washed with water, dried (Na$_2$SO$_4$) and evaporated. The residual oil was purified on a biotage cartridge (8 g) using dichloromethane-ethanol-0.88 ammonia (100:8:1) as eluent. The appropriate fractions were evaporated to give the title compound (0.11 g) LCMS RT=2.89 min.

xi) 4-{(1R)-2-[(6-{4-[3-(Cyclopentylsulfinyl)phenyl]butoxy}hexyl)amino]-1-hydroxyethyl}-2-(hydroxymethyl)phenol acetate A stirred solution of (1R)-2-[(6-{4-[3-(cyclopentylsulfinyl)phenyl]butoxy}hexyl)amino]-1-(2,2-dimethyl-4H-1,3-benzodioxin-6-yl)ethanol (0.1 g) in glacial acetic acid (5 ml) and water (0.2 ml) was heated at 82° C. for 40 min. The solution was evaporated to dryness to give the title compound as a clear oil (0.075 g). LCMS=2.61 min, ES+ve 532 (MH$^+$).

Example 2

4-{(1R)-2-[(6-{4-[3-(Cyclopentylsulfinyl)phenyl]butoxy}hexyl)amino]-1-hydroxyethyl}-2-(hydroxymethyl)phenol acetate (Isomer 1)

i) (5R)-3-(6-{4-[3-(Cyclopentylsulfinyl)phenyl]butoxy}hexyl)-5-(2,2-dimethyl-4H-1,3-benzodioxin-6-yl)-1,3-oxazolidin-2-one (Isomer 1)

Prepared using methods similar to those described in Example 1 ix)

Separation of diastereoisomers was achieved using a chiracel OD column (5 cm×20 cm) using heptane-ethanol (4:1) as eluent. The title compound was obtained as a clear oil (0.198 g). LCMS RT=3.69 min.

ii) (1R)-2-[(6-{4-[3-(Cyclopentylsulfinyl)phenyl]butoxy}hexyl)amino]-1-(2,2-dimethyl-4H-1,3-benzodioxin-6-yl)ethanol (Isomer 1)

Prepared using methods similar to those described in Example 1x)
LCMS RT=2.90 min.

iii) 4-{(1R)-2-[(6-{4-[3-(Cyclopentylsulfinyl)phenyl]butoxy}hexyl)amino]-1-hydroxyethyl}-2-(hydroxymethyl)phenol acetate (Isomer 1)

Prepared using methods similar to those described in Example 1 xi)
LCMS RT=2.60 min, ES+ve 532 (MH$^+$).

Example 3

4-{(1R)-2-[(6-{4-[3-(Cyclopentylsulfinyl)phenyl]butoxy}hexyl)amino]-1-hydroxyethyl)-2-(hydroxymethyl)phenol acetate (Isomer 2)

i) (5R)-3-(6-{4-[3-(Cyclopentylsulfinyl)phenyl]butoxy}hexyl)-5-(2,2-dimethyl-4H-1,3-benzodioxin-6-yl)-1,3-oxazolidin-2-one (Isomer 2)

Prepared using methods to those described in Example 1 ix)
LCMS RT=3.68 min.

ii) (1R)-2-[(6-{4-[3-(Cyclopentylsulfinyl)phenyl]butoxy}hexyl)amino]-1-(2,2-dimethyl-4H-1,3-benzodioxin-6-yl)ethanol (Isomer 2)

Prepared using methods similar to those described in Example 1x)
LCMS RT=2.89 min.

iii) 4-{(1R)-2-[(6-{4-[3-(Cyclopentylsulfinyl)phenyl]butoxy}hexyl)amino]-1-hydroxyethyl}-2-(hydroxymethyl)phenol acetate (Isomer 2)

Prepared using methods similar to those described in Example 1 xi)
LCMS RT=2.60 min, ES+ve 532 (MH+).

Example 4

4-{(1R)-2-[(6-{4-[3-(Cyclopentylsulfonyl)phenyl]butoxy}hexyl)amino]-1-hydroxyethyl}-2-(hydroxymethyl)phenol acetate i) (5R)-3-(6-{4-[3-(Cyclopentylsulfonyl)phenyl]butoxy}hexyl)-5-(2,2-dimethyl-4H-1,3-benzodioxin-6-yl)-1,3-oxazolidin-2-one 3-Chloroperoxybenzoic acid (0.088 g) was added to a stirred, cooled (ice-bath) solution of (5R)-3-(6-{4-[3-(cyclopentylsulfinyl)phenyl]butoxy}hexyl)-5-(2,2-dimethyl-4H-1,3-benzodioxin-6-yl)-1,3-oxazolidin-2-one (0.097 g) in DCM (10 ml). The solution was stirred for 0.5 h at room temperature. The solution was diluted with DCM and washed with 2N NaOH solution, water, dried (Na$_2$SO$_4$) and evaporated to give the title compound (0.085 g)
LCMS RT=3.78 min.

ii) (1R)-2-[(6-{4-[3-(Cyclopentylsulfonyl)phenyl]butoxy}hexyl)amino]-1-(2,2-dimethyl-4H-1,3-benzodioxin-6-yl)ethanol A stirred mixture of (5R)-3-(6-{4-[3-(Cyclopentylsulfonyl)phenyl]butoxy}hexyl)-5-(2,2-dimethyl-4H-1,3-benzodioxin-6-yl)-1,3-oxazolidin-2-one and potassium trimethyl silanolate (240 mg) in THF (6 ml) was heated to reflux for 1.5 h. The mixture was poured into phoshate buffer solution (pH 5) and extracted into DCM. The extracts were washed with water, dried (Na$_2$SO$_4$) and evaporated to give the title compound (120 mg). LCMS RT=2.93 min.

iii) 4-{(1R)-2-[(6-{4-[3-(Cyclopentylsulfonyl)phenyl]butoxy}hexyl)amino]-1-hydroxyethyl}-2-(hydroxymethyl)phenol acetate A stirred solution of (1R)-2-[(6-{4-[3-(Cyclopentylsulfonyl)phenyl]butoxy}hexyl)amino]-1-(2,2-dimethyl-4H-1,3-benzodioxin-6-yl)ethanol (110 mg) in glacial AcOH (5 ml) and water (0.3 ml) was heated at 85° C. for 40 min. The solution was evaporated to dryness and the residue was purified by Biotage™ column chromatography on silica using DCM-EtOH-ammonia (50:8:1) as eluent. The residue was dissolved in MeOH, treated with glacial AcOH and the solvent was removed to give the title compound (76 mg). LCMS RT=2.6 min ES+ve 548

Example 5

4-{(1R)-2-[(6-{4-[4-(Cyclopentylsulfonyl)phenyl]butoxy}hexyl)amino]-1-hydroxyethyl}-2-(hydroxymethyl)phenol acetate i) 1-{4-[(6-Bromohexyl)oxy]but-1-ynyl}-4-(cyclopentylsulfonyl)benzene

A stirred solution of 4-bromophenyl cyclopentyl sulfone (EP683172 A1) (0.5 g) and N,N-diisopropylethylamine (3.33 ml) in DMF (15 ml) was treated with dichlorobis(triphenylphosphine) palladium (II) (50 mg) and copper iodide (13.68 mg). The solution was heated to 70° under nitrogen and a solution of 4-[(6-bromohexyl)oxy]but-1-yne (DE 3513885 A1) and N,N-diisopropylethylamine (1.66 ml) in DMF (5 ml) was added dropwise. The mixture was stirred at 70° for 19 h. The reaction mixture was cooled to room temperature, poured onto water and extracted 3 times with EtOAc. The extracts were dried (MgSO$_4$) and evaporated in vacuo. The residual oil was purified on a silica SPE bond elut cartridge (100 g), using a gradient of 0% to 30% diethyl ether in cyclohexane (Gradmaster™). The appropriate fractions were evaporated to give the title compound (280 mg). LCMS RT=3.93 min ii) (1R)-2-{[6-({4-[4(Cyclopentylsulfonyl)phenyl]but-3-vnyl}oxy)hexyl]amino}-1-(2,2-dimethyl-4H-1,3-benzodioxin-6-yl)ethanol To a stirred solution of 1-{4-[(6-bromohexyl)oxy]but-1-ynyl}-4-(cyclopentylsulfonyl) benzene (280 mg) in DMF (10 ml) were added (1R)-2-amino-1-(2,2-dimethyl-4H-1,3-benzodioxin-6-yl)ethanol (WO 0266422 A1) (170 mg) and diisopropylethylamine (165 µl). The mixture was heated at 50° for 22 h before being allowed to cool to room temperature. The mixture was dissolved in EtOAC, washed with brine, dried (MgSO$_4$) and evaporated to dryness. The residual oil was purified on a silica bond elut SPE cartridge (10 g), gradient 0% to 30% [MeOH-aqueous ammonia (10:1)] in DCM (Gradmaster™). The appropriate fractions were evaporated to give the title compound (127 mg) LCMS RT=2.87 min iii) (1R)-2-[(6-{4-[4-(Cyclopentylsulfonyl)phenyl]butoxy}hexyl)amino]-1-(2,2-dimethyl-4H-1,3-benzodioxin-6-yl)ethanol A solution of (1R)-2-{[6-({4-[4-(cyclopentylsulfonyl)phenyl]but-3-ynyl}oxy)hexyl]amino]-1-(2,2-dimethyl-4H-1,3-benzodioxin-6-yl)ethanol (127 mg) in EtOAc (10 ml) was hydrogenated over a palladium on carbon catalyst (50% water by weight, 6.35 mg) for 19 h. The catalyst was removed iv) 4-{(1R)-2-[(6-{4-[4-(Cyclopentylsulfonyl)phenyl]butoxy}hexyl)amino]-1-hydroxyethyl}-2-(hydroxymethyl)phenol acetate Prepared using the method described in Example 1xi) LCMS RT=2.60 min, ES+ve 548 (MH)+

Example 6

4-((1R)-2-{[6-({4-[3-(Cyclohexylsulfonyl)phenyl]butyl}oxy)hexyl]amino}-1-hydroxyethyl)-2-(hydroxymethyl)phenol acetate i) 3-Bromophenyl cyclohexyl sulfide To a stirred solution of 3-bromobenzenethiol (5.00 g) in DMF (100 ml) was added cyclohexyl bromide (4.31 g) and potassium carbonate (7.31 g). The mixture was stirred at room temperature under nitrogen for 18 h. The reaction mixture was partitioned between 2N HCl and EtOAC. The organic phase was washed with brine and dried ($MgSO_4$). Filtration and removal of the solvent under reduced pressure gave the title compound (3.89 g). Tlc (silica) (4:1 cyclohexane-diethyl ether) Rf=0.90.

ii) 3-Bromophenyl cyclohexyl sulfone

A stirred solution of 3-bromophenyl cyclohexyl sulfide (3.89 g) in DCM (200 ml) under nitrogen was treated with meta-chloroperbenzoic acid (57% pure, 8.69 g), and stirred at room temperature for 1.5 h. The reaction mixture was poured into water and washed with aqueous sodium sulphite until no peracid remained. The organic phase was washed with brine and dried ($MgSO_4$). Filtration and removal of the solvent under reduced pressure gave the title compound (3.63 g). LCMS RT=3.33 min.

iii) 1-{4-[(6-Bromohexyl)oxy]-1-butyn-1-yl}-3-(cyclohexylsulfonyl)benzene

Prepared using method described in Example 5 i) LCMS RT=3.98 min.

iv) (1R)-2-{[6-({4-[3-(Cyclohexylsulfonyl)phenyl]-3-butyn-1-yl}oxy)hexyl]amino}-1-(2,2-dimethyl-4H-1,3-benzodioxin-6-yl)ethanol Prepared using method described in example 5 ii) LCMS RT=2.92 min.

v) (1R)-2-{[6-({4-[3-(Cyclohexylsulfonyl)phenyl]butyl}oxy)hexyl]amino}-1-(2,2-dimethyl-4H-1,3-benzodioxin-6-yl)ethanol Prepared using method described in example 5 iii) LCMS RT=2.94 min.

vi) 4-((1R)-2-{[6-({4-[3-(Cyclohexylsulfonyl)phenyl]butyl}oxy)hexyl]amino}-1-hydroxyethyl)-2-(hydroxymethyl)phenol acetate Prepared using the method described in Example 1xi) LCMS RT=2.69 min. ES+ve 561 (MH)+

Example 7

4-((1R)-2-{[6-({4-[3-(3-Cyclopenten-1-ylsulfonyl)phenyl]butyl}oxy)hexyl]amino}-1-hydroxyethyl)-2-(hydroxymethyl)phenol acetate i) 1-[(1-Allylbut-3-enyl)sulfonyl]-3-bromobenzene To a stirred solution of 3-bromophenyl methyl sulfone (Tet. Left. 1994, 35, 9063; 4.74 g) in THF (200 ml) at −78° under nitrogen was added a solution of lithium bis(trimethylsilyl)amide (19 ml, 1.06M in THF) dropwise. The mixture was stirred for 25 min before a solution of allyl bromide (2.44 g) in THF (10 ml) was added. The mixture was allowed to stir at −78° for 1.5 h then quenched with an aqueous solution of ammonium chloride. The product was extracted with EtOAc, and the organic phase washed with brine, dried ($MgSO_4$) and evaporated to dryness. The residual oil was purified on a silica SPE bond elut cartridge (100 g) using a gradient of 5%-40% diethyl ether in cyclohexane (Gradmaster™). The appropriate fractions were evaporated to give the title compound (1.66 g) LCMS RT=3.40 min.

ii) 4-[(6-Bromohexyl)oxy]-1-butene

A mixture of 1,6-dibromohexane (18.30 g), 3-butene-1-ol (2.15 ml), and tetrabutylammonium bromide (0.81 g) were stirred vigorously with 10N NaOH (25 ml) at room temperature under nitrogen for 18 h. The reaction mixture was partitioned between water and EtOAc. The organic phase was washed with brine, dried ($MgSO_4$), and evaporated to dryness. The residual oil was purified on a silica SPE bond elut cartridge (100 g). The excess 1,6-dibromohexane was eluted with cyclohexane. Elution with 5% diethyl ether in cyclohexane and removal of the solvent under reduced pressure gave the title compound (4.52 g). Tlc-silica (5% diethyl ether in cyclohexane) Rf=0.44.

iii) (5R)-3-[6-(3-Buten-1-yloxy)hexyl]-5-(2,2-dimethyl-4H-1,3-benzodioxin-6-yl)-1,3-oxazolidin-2-one To a solution of (5R-5-(2,2-dimethyl-4H-1,3-benzodioxin-6-yl)-1,3-oxazolidin-2-one (WO 0266422) (2.00 g) in DMF (25 ml) under nitrogen was added sodium hydride (60% dispersion in mineral oil, 0.38 g) and the mixture was stirred at room temperature for 15 min. A solution of 4[(6-bromohexyl)oxy]-1-butene (2.07 g) in DMF (5 ml) was added dropwise and the mixture stirred for 3 h. The reaction was quenched with water and partitioned between water and EtOAc. The organic phase was washed with brine, dried ($MgSO_4$), and evaporated to dryness. The residual oil was purified on a silica SPE bond elut cartridge (50 g) using a gradient of 10%-30% EtOAc in cyclohexane (Gradmaster™). The appropriate fractions were evaporated to give the title compound (2.66 g) LCMS RT=3.47 min.

iv) (5R)-5-(2,2-Dimethyl-4H-1,3-benzodioxin-6-yl)-3-(6-{[4-(3-{[1-(2-propen-1-yl)-3-buten-1-yl]sulfonyl}phenyl)butyl]oxy}hexyl)-1,3-oxazolidin-2-one To a solution of (5R)-3-[6-(3-buten-1-yloxy)hexyl]-5-(2,2-dimethyl-4H-1,3-benzodioxin-6-yl)-1,3-oxazolidin-2-one (1.00 g) in THF (2 ml) was added a 0.5M solution of 9-borabicyclo[3.3.1]nonane (9-BBN) in THF (6 ml). The solution was stirred at room temperature under nitrogen for 2 h. Tripotassium phosphate (1.05 g) in water (1.5 ml) was added followed by 1-[(1-allylbut-3-enyl)sulfonyl]-3-bromobenzene (0.78 g), palladium acetate (6 mg), and $PPh_3$ (13 mg). The mixture was heated at 600 with vigorous stirring for 22 h. The mixture was allowed to return to room temperature then partitioned between water and EtOAc. The organic phase was washed with brine, dried ($MgSO_4$), and evaporated to dryness. The residual oil was purified on silica SPE bond elut cartridge (50 g) using a gradient of 30%-50% EtOAc in cyclohexane (Gradmaster™). The appropriate fractions were evaporated to give the title compound (1.20 g) LCMS RT=3.91 min.

v) (5R)-3-[6-({4-[3-(3-Cyclopenten-1-ylsulfonyl) phenyl]butyl}oxy)hexyl]-5-(2,2-dimethyl-4H-1,3-benzodioxin-6-yl)-1,3-oxazolidin-2-one A solution of (5R)-5-(2,2-dimethyl-4H-1,3-benzodioxin-6-yl)-3-(6-{[4-(3-{[1-(2-propen-1-yl)-3-buten-1-yl] sulfonyl}phenyl)butyl]oxy}hexyl)-1,3-oxazolidin-2-one (0.5 g) in DCM (25 ml) was deoxygenated for 5 min. Benzylidene-bis(tricyclohexylphosphine)-dichlororuthenium (32 mg) was added and the mixture heated at reflux under nitrogen for 55 min. The reaction was allowed to cool and the residue was applied to a silica SPE bond elut cartridge (10 g). Elution using EtOAc-cyclohexane (2:3) gave the title compound (0.38 g).
LCMS RT=3.70 min.

vi) (1R)-2-{[6-([{4-[3-(3-Cyclopenten-1-ylsulfonyl) phenyl]butyl}oxy)hexyl]amino}-1-(2,2-dimethyl-4H-1,3-benzodioxin-6-yl)ethanol To a stirred solution of (5R)3-[6-({4-[3(3-cyclopenten-1-ylsulfonyl)phenyl]butyl}oxy) hexyl]-5-(2,2-dimethyl-4H-1, 3-benzodioxin-6-yl)-1,3-oxazolidin-2-one (360 mg) in THF (12 ml) was added potassium trimethylsilanolate (0.11 g) and the mixture heated at 700 for 2 h. Further potassium trimethylsilanolate was added (0.05 g), and again after 4 h. After 6 h the mixture was allowed to cool and partitioned between EtOAc and water. The organic phase was washed with brine, dried ($MgSO_4$), and evaporated to dryness. The residual oil was purified on silica SPE bond elut cartridge (10 g) using a gradient of MeOH in DCM (0-7%) (Gradmaster™). The appropriate fractions were evaporated to give the title compound (120 mg) LCMS RT=2.79 min.

vii) 4-((1R)-2-{[6-({4-[3-(3-Cyclopenten-1-ylsulfonyl)phenyl]butyl}oxy)hexyl]amino}-1-hydroxyethyl)-2-(hydroxymethyl)phenol acetate Prepared using the method described in Example 1xi) (PG 49791) LCMS RT=2.53 min, ES+ve 545 $(MH)^+$

Example 8

4-((1R)-2-{[6-({5-[3-(Cyclopentylsulfonyl)phenyl] pentyl}oxy)hexyl]amino}-1-hydroxyethyl)-2-(hydroxymethyl)phenol acetate i) 1-Bromo-3-(cyclopentylthio)benzene

Iodocyclopentane (3.93 ml) was added to a mixture of 3-bromobenzenethiol and potassium carbonate (5.4 g) in acetone (50 ml) and the reaction was stirred under nitrogen for 1.5 h. A further portion of iodocyclopentane (2 ml) was added and the mixture was stirred for 1 h. The solvent was evaporated and the residue was partitioned between water and EtOAc. he combined organic extracts were washed with NaOH (2N), brine and dried ($Na_2SO_4$). The resulting oil was purified using biotage™ chromatography on silica using cyclohexane as eluant to give the title compound (3.6 g). LCMS RT=4.1 min ii) 1-(Cyclopentylthio)-3-iodobenzene

To a solution of 1-(cyclopentylthio)-3-bromobenzene (3.6 g) in dry THF (40 ml) at −60° under nitrogen was added n-butyl lithium (10 ml, 1.6M in hexanes). After stirring for 15 min a solution of iodine (4.3 g) in dry THF (30 ml) was added dropwise and the solution was allowed to warm to 0°. Wet THF was added to the brown solution, followed by aqueous sodium sulphite. The resulting colourless solution was extracted with diethyl ether and the combined organic extracts were washed with water, brine and dried ($Na_2SO_4$). The solvent was evaporated and the residue was purified by column chromatography on silica using cydohexane as eluant. This gave the title compound (1.8 g). LCMS RT=4. 1 min iii) 1-(Cyclopentylsulfonyl)-3-iodobenzene

To a solution of the 1-(cyclopentylthio)-3-iodobenzene (1.8 g) in DCM (40 ml) at 0° was added m-chloroperbenzoic acid (4.3 g) portionwise. The mixture was stirred for 2 h at RT and the solution was washed with aqueous sodium sulphite solution. The organic phase was applied to a pad of alumina and was eluted using cyclohexane-EtOAc (1:1). This gave the title compound as a pale yellow foam (1.7 g). LCMS RT=3.3 min iv) (5R)-5-(2,2-Dimethyl-4H-1,3-benzodioxin-6-yl)-3-[6-(4-pentyn-1-yloxy)hexyl]-1,3-oxazolidin-2-one A solution of (5R)-5-(2,2-dimethyl-4H-1,3-benzodioxin-6-yl)-1,3-oxazolidin-2-one (Example 1vi) (500 mg) in DMF (15 ml) under nitrogen at 0° was treated with sodium hydride (60% dispersion in mineral oil, 96 mg) and the mixture stirred at 20° for 10 min. A solution of 6-bromohexyl 4-pentyn-1-yl ether (WO 02/066422) (545 mg) in DMF (1 ml) was added and the mixture stirred at 20° for 18 h. Phosphate buffer solution (pH 6.5) and water were added and the mixture was extracted with EtOAc. The extract was washed with water and dried ($Na_2SO_4$). Solvent evaporation in vacuo gave a residue, which was purified by flash chromatography on silica gel. Elution with EtOAc-PE (2:3) gave the title compound (700 mg). LCMS RT=3.48 min.

v) (5R)-3-[6-({5-[3-(Cyclopentylsulfonyl)phenyl]-4-pentyn-1-yl}oxy)hexyl]-5-(2,2-dimethyl-4H-1,3-benzodioxin-6-yl)-1,3-oxazolidin-2-one A solution of (5R)-5-(2,2-dimethyl-4H-1,3-benzodioxin-6-yl)-3-[6-(4-pentyn-1-yloxy)hexyl]-1,3-oxazolidin-2-one (207 mg) and 1-(cyclopentylsulfonyl)-3-iodobenzene (Example 8iii.) (202 mg) in MeCN (8 ml) and triethylamine (4 ml) was deoxygenated by bubbling a nitrogen stream through for 10 min. Copper (I) iodide (10 mg) and dichlorobis(triphenylphosphine)palladium (II) (18 mg) were added and the mixture stirred at 20° for 4 h. The solvent was evaporated in vacuo and the residues purified by using a SPE silica bond elut cartridge (10 g, silica). Elution with DCM (1vol), EtOAc- vi) (5R)-3-[6-({5-[3-(Cyclopentylsulfonyl)phenyl] pentyl}oxy)hexyl]-5-(2,2-dimethyl-4H-1,3-benzo-dioxin-6-yl)-1,3-oxazolidin-2-one A solution of (5R)-3-[6-({5-[3-(cyclopentylsulfonyl)phenyl]-4-pentyn-1-yl}oxy)hexyl]-5-(2,2-dimethyl-4H-1,3-benzodioxin-6-yl)-1,3-oxazolidin-2-one (215 mg) in EtOAc (10 ml) and EtOH (10 ml) was hydrogenated over platinum oxide (30 mg). When hydrogen uptake had ceased the mixture was filtered through celite and the solvent was evaporated in vacuo to give the title compound (200 mg). LCMS RT=3.83 min.

vii) (1R)-2-{[6-({5-[3-Cyclopentylsulfonyl)phenyl] pentyl}oxy)hexyl]amino}-1-(2,2-dimethyl-4H-1,3-benzodioxin-6-yl)ethanol Prepared using methods similar to those described in Example 1x.
LCMS RT=2.93 min.

viii) 4-((1R)-2-{[6-({5-[3-(Cyclopentylsulfonyl) phenyl]pentyl}oxy)hexyl]amino}-1-hydroxyethyl)-2-(hydroxymethyl)phenol acetate Prepared using methods similar to those described in Example 1xi.
LCMS RT=2.67 min ES+ve 562 (MH)+.

Example 9

4-((1R)-2-{[7-({3-[3-(Cyclopentylsulfonyl)phenyl] propyl}oxy)heptyl]amino}-1-hydroxyethyl)-2-(hydroxymethyl)phenol acetate i) (5R)-5-(2,2-Dimethyl-4H-1,3-benzodioxin-6-yl)-3-[7-(2-propyn-1-yloxy)heptyl]-1,3-oxazolidin-2-one Prepared using methods similar to those described in Example 8iv.
LCMS RT=3.44 min.

ii) (5R)-3-7-({3-[3-(Cyclopentylsulfonyl)phenyl-2-propyn-1-yl}oxy)heptyl]-5-(2,2-dimethyl-4H-1,3-benzodioxin-6-yl)-1,3-oxazolidin-2-one Prepared using methods similar to those described in Example 8v.
LCMS RT=3.75 min.

iii) (5R)-3-[7-({3-[3-(Cyclopentylsulfonyl)phenyl] propyl}oxy)heptyl]-5-(2,2-dimethyl-4H-1,3-benzo-dioxin-6-yl)-1,3-oxazolidin-2-one Prepared using methods similar to those described in Example 8vi.
LCMS RT=3.76 min.

iv) (1R)-2-{[7-({3-[3-(Cyclopentylsulfonyl)phenyl] propyl}oxy)heptyl]amino}-1-(2,2-dimethyl-4H-1,3-benzodioxin-6-yl)ethanol Prepared using methods similar to those described in Example 1x.
LCMS RT=2.86 min.

v) 4-((1R)-2-{[7-({3-[3-(Cyclopentylsulfonyl)phe-nyl]propyl}oxy)heptyl]amino}-1-hydroxyethyl)-2-(hydroxymethyl)phenol acetate Prepared using methods similar to those described in Example 1xi.
LCMS RT=2.59 min ES+ve 548 (MH)+.

Example 10

4-((1R)-2-{[6-({4-[3-(Cyclopentylsulfonyl)-5-meth-ylphenyl]butyl}oxy)hexyl]amino}-1-hydroxyethyl)-2-(hydroxymethyl)phenol acetate i) 1-(Cyclopentylthio)-3-iodo-5-methylbenzene

A mixture of 1,3-diiodo-5-methylbenzene (2.00 g), tris (dibenzylideneacetone)dipalladium (0) (20 mg), bis(diphe-nylphosphino)ferrocene (22 mg), triethylamine (1.5 ml) and 1-methyl-2-pyrrolidinone (3 ml) were stirred at to 20° under nitrogen for 1 h. Cyclopentanethiol (0.15 ml) was added and the mixture was heated to 60° for 18 h. The mixtue was cooled to 20° and was treated with phosphate buffer solution (pH 6.5) and water. The mixture was extracted with EtOAc and the extract dried ($Na_2SO_4$). Solvent evaporation in vacuo gave a residue which was purified by Flashmaster™ chromatography (silica, 70 g). Elution with cyclohexane gave the title compound (444 mg). LCMS RT=4.21 min.

ii) 1-(Cyclopentylsulfonyl)-3-iodo-5-methylbenzene

A solution of 1-(cyclopentylthio)-3-iodo-5-methylben-zene (440 mg) in DCM (20 ml) at 20° under nitrogen was treated with 3-chloroperoxybenzoic acid (1.046 g, 57-86% pure) and the mixture stirred at 20° for 2 h. 0.5M Aqueous sodium metabisulphite solution was added and the mixture was vigorously stirred at 20° for 18 h. The layers were separated and the organic phase washed with 0.5M aqueous sodium metabisulphite solution. The organic phase was dried ($Na_2SO_4$) and the solvent evaporated in vacuo. The residue was purified using a SPE bond elut cartridge (2×10 g, silica). Elution with DCM (5 vols) gave the title compound (425 mg). LCMS RT=3.36 min.

iii) (5R)-3-[6-({4-[3-(Cyclopentylsulfonyl)-5-meth-ylphenyl]-3-butyn-1-yl}oxy)hexyl]-5-(2,2-dimethyl-4H-1,3-benzodioxin-6-yl)-1,3-oxazolidin-2-one Prepared using methods similar to those described in Example 8v using (5R)-3-[6-(but-3-ynyloxy)hexyl]-5-(2,2-dimethyl-4H-1,3-benzodioxin-6-yl)-1,3-oxazolidin-2-one (WO0266422).
LCMS RT=3.81 min.

iv) (5R)-3-[6-({4-[3-(Cyclopentylsulfonyl)-5-methylphenyl]butyl}oxy)hexyl]-5-(2,2-dimethyl-4H-1,3-benzodioxin-6-yl)-1,3-oxazolidin-2-one Prepared using methods similar to those described in Example 8vi.
LCMS RT=3.86 min.

v) (1R)-2-{[6-({4-[3-(Cyclopentylsulfonyl)-5-methylphenyl]butyl}oxy)hexyl]amino}-1-(2,2-dimethyl-4H-1,3-benzodioxin-6-yl)ethanol Prepared using methods similar to those described in Example 1x.
LCMS RT=2.91 min.

vi) 4-((1R)-2-{[6-({4-[3-(Cyclopentylsulfonyl-5-methylphenyl]butyl}oxy)hexyl]amino}-1-hydroxyethyl)-2-(hydroxymethyl)phenol acetate (salt)

Prepared using methods similar to those described in Example 1xi.
LCMS RT=2.66 min ES+ve 562 (MH)+.

Example 11

N-[5-((1R)-2-{[6-({4-[3-(Cyclopentylsulfonyl)phenyl]butyl}oxy)hexyl]amino}-1-hydroxyethyl)-2-hydroxyphenyl]methanesulfonamide i) 1-{4-[(6-Bromohexyl)oxy]-1-butyn-1-yl}-3-(cyclopentylsulfonyl)benzene

A solution of 4-[(6-bromohexyl)oxy]-1-butyne (DE 3513885 A1) (288.9 mg) and 1-(cyclopentylsulfonyl)-3-iodobenzene (500 mg) in MeCN (20 ml) and triethylamine (345 µl) was treated with copper iodide (11.78 mg) and dichlorobis(triphenylphosphine)palladium(II) (43.4 mg) and stirred at room temperature for 3 h. The reaction mixture was partitioned between EtOAc and water, the organic phase was dried (MgSO4) and concentrated in vacuo. The mixture was purified by column chromatography (SPE bond elut, gradient 0 to 40% diethyl ether in cyclohexane) to afford the title compound.
LCMS RT=3.83 min 441(M+NH4)+ ii) 1-{4-[(6-Bromohexyl)oxy]butyl}-3-(cyclopentylsulfonyl)benzene

To an evacuated flask, containing palladium on carbon [50% water by weight] (43 mg) was added a solution of 1{4-[(6-bromohexyl)oxy]-1-butyn-1-yl}-3-(cyclopentylsulfonyl) benzene (304 mg) in EtOAc (10 ml). The mixture was hydrogenated for 19 h. The catalyst was filtered off and the filtrate was concentrated in vacuo to afford title compound.
LCMS RT=3.92 min iii) N-{5-(Bromoacetyl)-2-[(phenylmethyl)oxy]phenyl}-N-(phenylmethyl)methanesulfonamide A solution of N-{5-acetyl-2-[(phenylmethyl)oxy]phenyl}-N-(phenylmethyl) methanesulfonamide (J. Med Chem 1977, 20, 687-92) (1.18 g) in THF (50 ml) was treated with phenyltrimethylammonium tribromide (1.08 g) at <10° and stirred for 6 h. The reaction mixture was quenched with chilled water and then filtered. The filtrate was partitioned between diethyl ether and water, the organic phase was dried (MgSO4) and the solvent was removed in vacuo. The mixture was purified by column chromatography on silica (SPE bond elut, gradient 0 to 45% EtOAc-cyclohexane) to afford the title compound.
LCMS RT=3.48 min iv) N-{5-((1R)-1-Hydroxy-2-{[(1S)-2-hydroxy-1-phenylethyl]amino}ethyl)-2-[(phenylmethyl)oxy]phenyl}-N-(phenylmethyl)methanesulfonamide A solution of N-{5-(bromoacetyl)-2-[(phenylmethyl)oxy]phenyl}-N-(phenylmethyl) methanesulfonamide (570 mg) in THF (15 ml) was treated with N,N-diisopropylethylamine (0.41 ml) and (S)-(+)-2-phenylglycinol (191.8 mg). The mixture was stirred at room temperature for 5 h. The solvent was removed in vacuo and the resulting solid was suspended in dry MeOH (15 ml). The resulting suspension was cooled to 0°, treated with calcium carbonate (359 mg) and stirred for 0.5 h. The reaction mixture was treated with NaBH4 (88.8 mg), portionwise at 0° and was then allowed to warm to room temperature and stirred for 64 h. The mixture was concentrated in vacuo and the residue was partitioned between EtOAc and water. The organic phase was dried (MgSO4) and concentrated in vacuo. The mixture was purified by column chromatography (SPE, gradient 0 to 15% [MeOH-ammonia (10:1)] in DCM) to afford the title compound (360 mg).
LCMS RT 2.75 min v) N-{5-[(1R)-2-Amino-1-hydroxyethyl]-2-hydroxyphenyl}methanesulfonamide

To an evacuated flask containing palladium hydroxide (70.8 mg) and palladium on carbon [50% water by weight] (70.8 mg) was added a solution of N-{5-((1R)-1-hydroxy-2-{[(1S)-2-hydroxy-1-phenylethyl]amino}ethyl)-2-[(phenylmethyl)oxy]phenyl}-N-(phenylmethyl)methanesulfonamide (354 mg) in EtOH (15 ml) and AcOH (3 ml). The mixture was hydrogenated for 19 h. The catalysts were filtered off and the filtrate concentrated in vacuo. The mixture was purified by column chromatography (Oasis cartridge, 0 to 50% MeOH in water) to afford the title compound. LCMS RT=0.35 min vi) N-[5-((1R)-2-{[6-({4-[3-(cyclopentylsulfonyl)phenyl]butyl}oxy)hexyl]amino}-1-hydroxyethyl)-2-hydroxyphenyl]methanesulfonamide N-{5-[(1R)-2-Amino-1-hydroxyethyl]-2-hydroxyphenyl}methanesulfonamide (33.2 mg) was added to a solution of 1-{4-[(6-bromohexyl)oxy]butyl}-3-(cyclopentylsulfonyl)benzene (Example 1v.) (50 mg) in DMF (5 ml). The reaction mixture was treated with N,N-diisopropylethylamine (29.3 µl) and stirred at room temperature for 113 h. The reaction mixture was partitioned between EtOAc and water and the organic extracts were washed with ammonium chloride, dried (MgSO4) and concentrated in vacuo. The residue was purified by column DCM) to afford the title compound. LCMS RT=2.73 min 610(M+H)+

Example 12

4-((1R)-2-{[6-({4-[3-(Cyclopentylsulfonyl)phenyl]butyl}oxy)hexyl]amino}-1-hydroxyethyl)-2-fluorophenol i) 2-Azido-1-[4-(benzyloxy)-3-fluorophenyl]ethanone

A solution of 2-bromo-1-[4-(benzyloxy)-3-fluorophenyl] ethanone (J. Med. Chem. 1980, 23, 738-744) (1 g) in dry DMF (2.5 mL) was cooled to 150 and treated portionwise with sodium azide (220 mg). After complete addition the reaction mixture was stirred for a further 1 h. The reaction mixture was partitioned between EtOAc and water. The organic phase was washed with water and the combined aqueous phase back extracted with EtOAc. The combined organic phases were washed with sat. $NaHCO_{3(aq)}$ three times and the combined washes back extracted with EtOAc. The combined organic phase was washed with brine, dried ($MgSO_4$) and concentrated in vacuo. The residue was purified by column chromatography on silica, eluting with hexane-EtOAc (4:1 and 2:1) to give the title compound (810 mg). LCMS RT=3.61 min.

ii) (1R)-2-Azido-1-[4-(benzyloxy)-3-fluorophenyl]ethanol

Borane-dimethylsulphide solution in THF (2M, 0.03 mL) was added to a solution of (R)-2-methyl-CBS-oxazaborolidine in toluene (1M, 0.06 mL) at 0° with stirring. The reaction mixture was stirred for 15 min prior to the dropwise addition of a solution of 2-azido-1-[4-(benzyloxy)-3-fluorophenyl]ethanone (100 mg) in THF. Further Borane-dimethylsulphide in THF (2M, 0.03 mL) was added dropwise and the reaction mixture stirred at 0° for 2 h. 2M $HCl_{(aq)}$ (2 mL) was added dropwise and the reaction mixture stirred for 10 min prior to partitioning the reaction mixture between diethyl ether and water. The organic phase was washed twice with 2M $HCl_{(aq)}$, three times with sat. $NaHCO_{3(aq)}$, water and brine. The organic phase was dried and concentrated in vacuo. The residue was purified by column chromatography on silica gel, eluting with DCM to give the title compound (470 mg). LCMS RT=3.36 min.

ii (1R)-2-Amino-1-[4-(benzyloxy)-3-fluorophenyl]ethanol

A solution of (1R)-2-azido-1-[4-(benzyloxy)-3-fluorophenyl]ethanol (410 mg) in THF (8 mL) and water (2 mL) was treated with $PPh_3$ (410 mg) and stirred for 1 h prior to addition of a further portion of $PPh_3$ (220 mg). After stirring for a further 4 h the reaction mixture was concentrated in vacuo and the residue partitioned between EtOAc and water. The organic phase was washed three times with 5% $NaHCO_{3(aq)}$, dried ($MgSO_4$) and concentrated in vacuo. The residue was purified by chromatography on silica gel, eluting with DCM, 1% MeOH in DCM, 2% MeOH in DCM, 5% MeOH containing 0.5% $Et_3N$ in DCM, and finally 20% MeOH containing 1% $Et_3N$ in DCM) to give the title compound (260 mg). LCMS RT=2.16 min.

iv) (1R)-2-{[6-({4-[3-(Cyclopentylsulfonyl)phenyl]butyl}oxy)hexyl]amino}-1-{3-fluoro-4-[(phenylmethyl)oxy]phenyl}ethanol Prepared similarly to example 11(vi) from (1R)-2-Amino-1-[4-(benzyloxy)-3-fluorophenyl]ethanol to give the title compound. LCMS RT=3.15 min v) 4-((1R)-2-{[6-({4-[3-(Cyclopentylsulfonyl)phenyl]butyl}oxy)hexyl]amino}-1-hydroxyethyl)-2-fluorophenol To an evacuated flask containing palladium on carbon [50% water by weight] was added a solution of (1R)-2-{[6-({4-[3-(cyclopentylsulfonyl)phenyl]butyl}oxy)hexyl]amino)-1-{3-fluoro-4-[(phenylmethyl)oxy]phenyl}ethanol (37 mg) in EtOAc (8 ml) and AcOH (2 ml). The reaction mixture was hydrogenated for 4 h. The catalyst was filtered off and the filtrate concentrated in vacuo to give the title compound. LCMS RT=2.60 min 535(M+H)+

Example 13

6-{2-[(6-{4-[3-(Cyclopentylsulfonyl)phenyl]butoxy}hexyl)amino]-1-hydroxyethyl}-2-(hydroxymethyl)pyridin-3-ol acetate i) 2-[(6-{4-[3-(Cyclopentylsulfonyl)phenyl]butoxy}hexyl)amino]-1-(2-phenyl-4H-1,3]dioxino[5,4-b]pyridin-6-yl)ethanol Prepared using methods similar to those described in example 11 vi) using 2-amino-1-(2-phenyl-4H-[1,3]dioxino[5,4-b]pyridin-6-yl)ethanol (EP220054A2) to afford the title compound. LCMS RT=2.95 min ii) 6-{2-[(6-{4-[3-(Cyclopentylsulfonyl)phenyl]butoxy}hexyl)amino]-1-hydroxyethyl}2-(hydroxymethyl)pyridin-3-ol A solution of 2-[(6-{4-[3-(cyclopentylsulfonyl)phenyl]butoxy}hexyl)amino]-1-(2-phenyl-4H-[1,3]dioxino[5,4-b]pyridin-6-yl)ethanol (61 mg) in water (5 ml) and glacial acetic acid (5 ml) was heated under reflux for 0.5 h. The reaction mixture was concentrated in vacuo to afford the title compound. LCMS RT=2.63 min 548(M+H)+

Example 14

5{(1R)-2-[(6-{4-[3-(Cyclopentylsulfonyl)phenyl]butoxy}hexyl)amino]-1-hydroxyethyl}-8-hydroxy-3,4-dihydroquinolin-2(1H)-one acetate i) 5-[(1R)-2-(Benzylamino)-1-hydroxyethyl]-8-(benzyloxy)quinolin-2(1H)-one 8-(Benzyloxy)-5-[(2R)-oxiran-2-yl]quinolin-2(1H)-one (0.102 g) (WO 9525104), was dissolved in benzylamine (0.5 ml) and heated in a microwave oven for 15 min at 150°. Excess benzylamine was removed by evaporation on a rotary evaporator and the residue was purified on a silica SPE bond elut cartridge using MeOH/DCM-0.880 ammonia mixtures, to give the title compound (106 mg). LCMS RT=2.30 min ii) 5-{(1R)-2-[[6-({4-[3-(Cyclopentylsulfonyl)phenyl]butyl}oxy)hexyl](phenylmethyl)amino]-1-hydroxyethyl}-8-[(Phenylmethyl)oxy]-2(1H)-quinolinone 5-[(1R)-2-(Benzylamino)-1-hydroxyethyl]-8-(benzyloxy)quinolin-2(1H)-one (40 mg) was dissolved in MeCN (2 ml). N,N,-diisopropylethylamine (0.03 ml) and 1-{4-[(6-bromohexyl)oxy]butyl}-3-(cyclopentylsulfonyl)benzene (Example 1v) (30 mg) were added and the reaction mixture was heated at 80° under nitrogen for 48 h. The mixture was then diluted with water and extracted with EtOAc. The organic phases were combined, dried ($MgSO_4$), and evaporated in vacuo. The residue was purified on a silica SPE bond elut cartridge, eluting with EtOAc-cyclohexane mixtures, to give the title compound, (13 mg)

LCMS RT=3.1 min iii) 5-{(1R)-2-[(6-{4-[3-(Cyclopentylsulfonyl)phenyl]butoxy}hexyl)amino]-1-hydroxyethyl}-8-hydroxyquinolin-2(1H)-one acetate 5-(1R)-2-[[6-(4-[3-(Cyclopentylsulfonyl)phenyl]butyl}oxy)hexyl](phenylmethyl)amino]-1-hydroxyethyl}-8-[(phenylmethyl)oxy]-2(1H)-quinolinone (13 mg) was dissolved in EtOH (10 ml) and glacial acetic acid (0.5 ml) added. The solution was hydrogenated using 10% palladium on carbon (50% water by weight, 4 mg) and 20% palladium hydroxide on carbon (4 mg) for 20 h. The catalyst was removed by filtration and the filtrate was evaporated in vacuo. The residue was purified on an isolute aminopropyl cartridge (2 g), eluting with MeOH-DCM mixtures. Evaporation of the appropriate fractions with AcOH gave a mixture of the title compound, (4 mg). LCMS RT=2.52 min ES+ve 585 (MH)$^+$ and 5-{(1R)-2-[(6-4-[3-(Cyclopentylsulfonyl)phenyl]butoxy}hexyl)amino]-1-hydroxyethyl}8-hydroxy-3,4-dihydroquinolin-2(1H)-one acetate
LCMS RT=2.52 min, ES+ve 587 (MH)$^+$

Example 15

5-(1R)-2-[(6-{4-[3-(Cyclopentylsulfonyl)phenyl]butoxy}hexyl)amino]-1-hydroxyethyl}-2-hydroxyphenylformamide acetate i) N-Benzyl-6-{4-[3-(cyclopentylsulfonyl)phenyl]butoxy}hexan-1-amine

1-{4-[(6-Bromohexyl)oxy]butyl}-3-(cyclopentylsulfonyl)benzene (Example 11ii) (50 mg) was dissolved in benzylamine (0.5 ml), and heated in a microwave oven at 150° for 10 min. Excess benzylamine was removed in vacuo and the residue purified on a silica SPE bond elut cartridge, eluting with EtOAc-cyclohexane mixtures, to give the title compound, (40 mg) LCMS RT=2.74 min ii) 5-{(1R)-2-[Benzyl(6-{4-[3-(cyclopentylsulfonyl)phenyl]butoxy}hexyl)amino]-1-hydroxyethyl}-2-(benzyloxy)phenylformamide N-Benzyl-6-{4-[3-(cyclopentylsulfonyl)phenyl]butoxy}hexan-1-amine (40 mg) was dissolved in dry THF (0.25 ml) and {5-[(2R)-2-oxiranyl]-2-[(phenylmethyl)oxy]phenyl}formamide (23 mg) (Organic Process Research & Development 1998, 2, 96-99), added. The reaction mixture was heated in a microwave oven for 3 h at 150°. The solvent was removed and the residue purified on a silica SPE bond elut cartridge, eluting with EtOAc-cyclohexane mixtures to give the title compound, (17 mg) LCMS RT=3.1 min iii) 5{(1R)-2-[(6-{4-[3-(Cyclopentylsulfonyl)phenyl]butoxy}hexyl)amino]-1-hydroxyethyl}-2-hydroxyphenylformamide acetate 5-{(1R)-2-[Benzyl(6-{4-[3-(cyclopentylsulfonyl)phenyl]butoxy}hexyl)amino]-1-hydroxyethyl}-2-(benzyloxy)phenylformamide (17 mg) was dissolved in EtOH (10 ml) and glacial acetic acid (1 ml) added. The solution was hydrogenated using 10% palladium on carbon (50% water by weight, 7 mg) and 20% palladium hydroxide on carbon (7 mg) for 20 h. The catalyst was removed by filtration and the filtrate was evaporated in vacuo. The residue was purified on an isolute aminopropyl cartridge (2 g), eluting with MeOH-DCM mixtures. Evaporation of the appropriate fractions with AcOH gave the title compound, (5 mg) LCMS RT=2.53 min, ES+ve 561 (MH)$^+$

Example 16 i) 4-{(1R)-2-[(6-{4-[3-(Cyclopentylsulfonyl)phenyl]butoxy}hexyl)amino]-1-hydroxyethyl}-2-(hydroxymethyl)phenol 4-{(1R)-2-[(6-{4-(3-(Cyclopentylsulfonyl)phenyl]butoxy}hexyl)amino]-1-hydroxyethyl}-2-(hydroxymethyl)phenol acetate (3.19 g) (Example 4iii.) was purified by chromatography on a biotag™ column of silica using DCM-MeOH-0.880 ammonia (100:8:1 followed by 90:10:1) to give the title compound (1.6 g). LCMS RT=2.6 min

Example 17

The following salts of the compound of Example 16 were prepared as described below:

L-Aspartate salt: A hot solution of L-aspartic acid (2.55 g) in water (250 ml) was added to a solution of the free base (10 g) in ethanol (100 ml). The resulting solution was evaporated to an oil which was re-evaporated twice with water to ensure removal of ethanol affording the title salt as a gum.

$^1$H NMR (DMSO, 400 MHz) δ ppm 1.27 (m, 4H), 1.42-1.66 (m, 12H), 1.71-1.88 (m, 4H), 2.29 (dd, J=6.7, 16.0 Hz, 1H), 2.55 (dd, J=7.5, 16.0 Hz, 1H), 2.76 (m, 6H), 3.31 (t, J=6.4 Hz, 2H), 3.34 (t, J=6.4 Hz, 2H), 3.50 (t, J=7.1 Hz, 1H), 3.75 (m, 1H), 4.46 (s, 2H), 4.68 (dd, J=3.4, 9.5 Hz, 1H), 6.73 (d, J=8.2 Hz, 1H), 7.01 (dd, J=2.0, 8.2 Hz, 1H), 7.29 (d, J=2.0 Hz, 1H), 7.56 (m, 2H), 7.69 (m, 2H).

Sulfamate salt: A solution of sulfamic acid (1.86 g) in water (50 ml) was added to a solution of the free base (10 g) in ethanol (100 ml). The resulting solution was evaporated to an oil which was re-evaporated twice with water to ensure removal of ethanol affording the title salt as a gum.

$^1$H NMR (DMSO, 400 MHz) δ ppm 1.28 (m, 4H), 1.43-1.67 (m, 12H), 1.71-1.89 (m, 4H), 2.71 (t, J=7.3 Hz, 2H), 2.92 (m, 3H), 3.03 (dd, J=2.7, 12.5 Hz, 1H), 3.32 (t, J=6.4 Hz, 2H), 3.35 (t, J=6.4 Hz, 2H), 3.76 (m, 1H), 4.48 (d, J=4.8 Hz, 2H), 4.56 (s, br, 2H), 4.79 (d, br J=10.1 Hz, 1H), 5.03 (t, J=5.3 Hz, 1H), 5.97 (s, br, 1H), 6.75 (d, J=8.2 Hz, 1H), 7.05 (dd, J=2.1, 8.2 Hz, 1H), 7.33 (d, J=2.1 Hz, 1H), 7.56 (m, 2H), 7.69 (m, 2H), 8.44 (s, br, 2H), 9.43 (s, 1H).

Napthalene-2-sulfonate salt: A solution of the free base (55 mg) in propan-2-ol (0.5 ml) was added to napthalene-2-sulfonic acid hydrate (27 mg) pre-weighed into a vial. The mixture was warmed to give a solution then cooled and left to stir at room temperature for 2 hours. The resulting solid was isolated by filtraton, washed with a little propan-2-ol and dried at 50° C. under vacuum, to give crystals of the title compound.

$^1$H NMR (DMSO, 400 MHz) δ ppm 1.27 (m, 4H), 1.43-1.66 (m, 12H), 1.71-1.89 (m, 4H), 2.71 (t, J=7.6 Hz, 2H), 2.91 (m, 3H), 3.03 (m, 1H), 3.31 (t, J=6.6 Hz, 2H), 3.35 (t, J=6.6 Hz, 2H), 3.76 (m, 1H), 4.48 (s, 2H), 4.76 (dd, J=2.5, 10.5 Hz, 1H), 5.98 (s, br, 1H), 6.75 (d, J=8.2 Hz, 1H), 7.05 (dd, J=2.2, 8.2 Hz, 1H), 7.33 (d, J=2.2 Hz, 1H), 7.52 (m, 2H), 7.56 (m, 2H), 7.69 (m, 2H), 7.72 (d, J=1.8 Hz, 1H), 7.86 (d, J=8.7 Hz, 1H), 7.90 (m, 1H), 7.97 (m, 1H), 8.14 (s, 1H), 8.42 (s, br, 2H), 9.42 (s, 1H).

Figure 3:
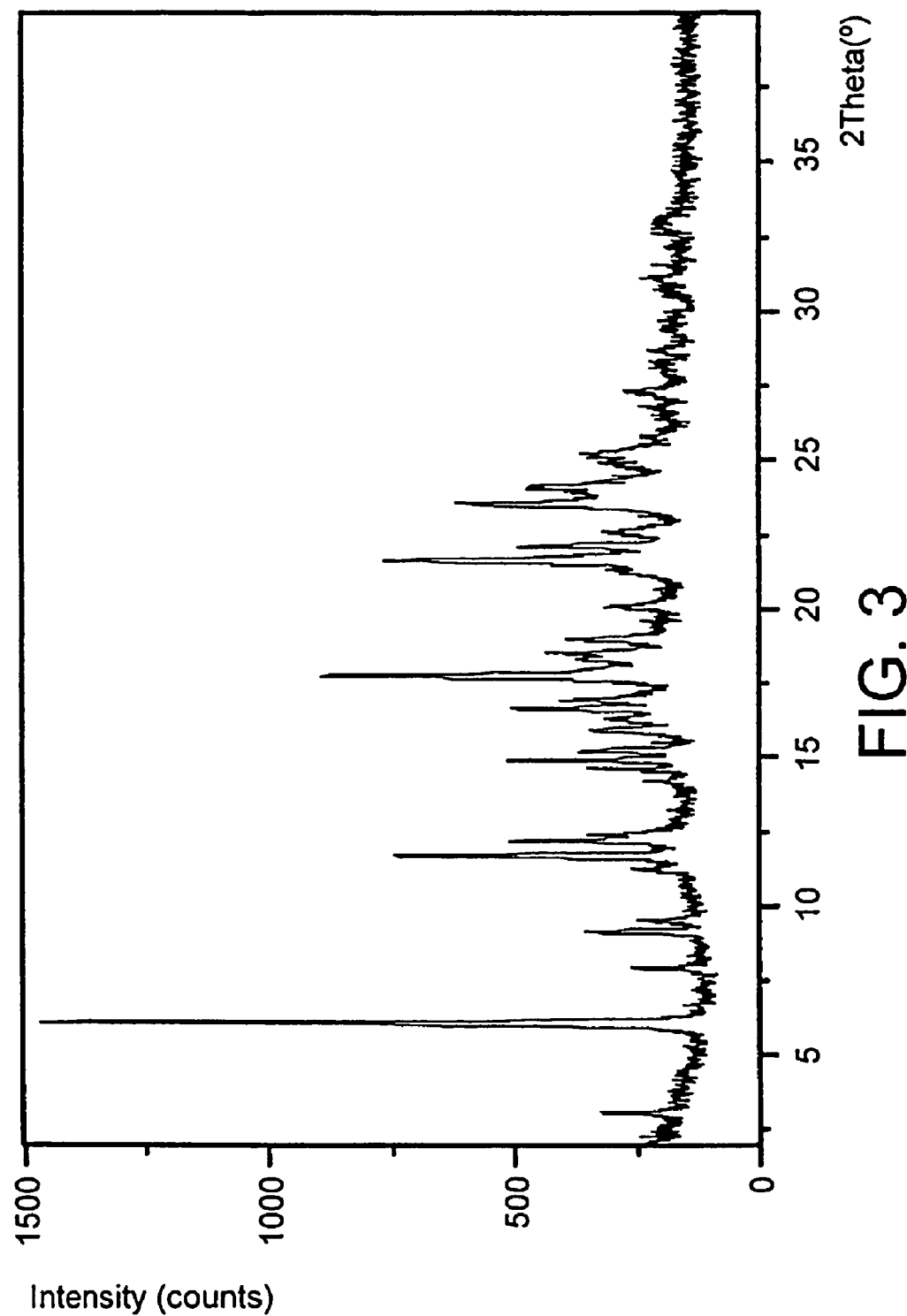
FIG. 3 shows an X-ray powder diffraction pattern of the naphthalene-2-sulfonate salt of 4{(1R)-2-[(6-{4-[3-(cyclopentylsulfonyl)phenyl]butoxy}hexyl)amino]-1-hydroxyethyl}-2-(hydroxymethyl)phenol.

The XRPD pattern of this product is shown in FIG. 3.

Example 18

The following salts of the compound of Example 16 were prepared as described below.

i) 4-{(1R)-2-[(6-{4-[3-(Cyclopentylsulfonyl)phenyl]butoxy}hexyl)amino]-1-hydroxyethyl}-2-(hydroxymethyl)phenol 4-methylbenzenesulfonate A solution of 4-{(1R)-2-[(6-{4-[3-(cyclopentylsulfonyl)phenyl]butoxy}hexyl)amino]-1-hydroxyethyl}-2-(hydroxymethyl)phenol (≈25 mg) in MeOH (0.45 ml) was added to p-toluene sulphonic acid (9.5 mg) and the resulting solvent was removed. EtOAc (0.45 ml) was added and the resulting mixture was agitated in a mini-reactor shaker block while alternately heating and cooling over 4 days. The precipitate was collected to give crystals of the title compound δ (CD$_3$OD) 7.74-7.67 (4H, m), 7.58-7.50 (2H, m), 7.34 (1H, d), 7.22 (2H, 0.5AA'BB'), 7.15 (1H, dd), 6.78 (1H, d), 4.85 (1H, dd), 4.63 (2H, s), 3.66 (1H, m), 3.47-3.37 (4H, 2xt), 3.14-2.97 (4H, 2xm), 2.75 (2H, t), 2.35 (3H, s) 2.03-1.35 (20H, 5xm)

ii) 4-{(1R)-2-[(6-{4-[3-(Cyclopentylsulfonyl)phenyl]butoxy}hexyl)amino]-1-hydroxyethyl}-2-(hydroxymethyl)phenol 4-chlorobenzene sulfonate 4-Chlorobenzene sulfonic acid (19 mg) was added to a solution of 4-{(1R)-2-[(6-{4-[3-(cyclopentylsulfonyl)phenyl]butoxy}hexyl)amino]-1-hydroxyethyl}-2-(hydroxymethyl)phenol (55 mg) (dissolved by gentle warming) in propan-2-ol (0.5 ml) at 21°. After a few minutes crystals had separated out. These were collected, and rinsed with propan-2-ol to give crystals of the title compound, δ (DMSO-d$_6$) 9.40 (1H,s), 8.42 (2H, br s), 7.72-7.67 (2H, m), 7.62-7.55 (4H, m), 7.38 (2H, m), 7.32 (1H, d, J=2 Hz), 7.05 (1H, dd, J 2,8 Hz), 6.75 (1H, d, J=8 Hz), 5.97 (1H, br s), 5.00 (1H, v br s), 4.76 (1H, br d, J=9 Hz), 4.49 (2H, s), 3.75 (1H m), 3.32 (4H, partially obscured t), 3.10-2.87 (4H, 2m), 2.71 (2H, t, J=7 Hz), 1.90-1.25 (20H, m).

The XRPD pattern of this product is shown in FIG. 1.

iii) 4-{(1R)-2-[(6-{4-[3-(Cyclopentylsulfonyl)phenyl]butoxy}hexyl)amino]-1-hydroxyethyl}-2-(hydroxymethyl)phenol 4-bromobenzene sulfonate This was prepared similarly to example 18 (ii) above, to give crystals of the title compound. δ (DMSO-d$_6$) 9.40 (1H, brs), 8.35 (2H, v br s), 7.72-7.68 (2H, m), 7.59-7.55 (2H, m), 7.52 (4H, m), 7.33 (1H, d, J=2 Hz), 7.05 (1H, dd, J 2,8 Hz), 6.75 (1H, d, J=8 Hz), 5.95 (1H, br s), 5.01 (1H, t, J=5 Hz)), 4.75 (1H, br d, J=10 Hz), 4.48 (2H, d, J=5 Hz), 3.75 (1H m), 3.38-3.28 (4H, partially obscured 2t), 3.05-2.87 (4H, 2m), 2.71 (2H, t, J=7 Hz), 1.90-1.25 (20H, m).

Figure 4:
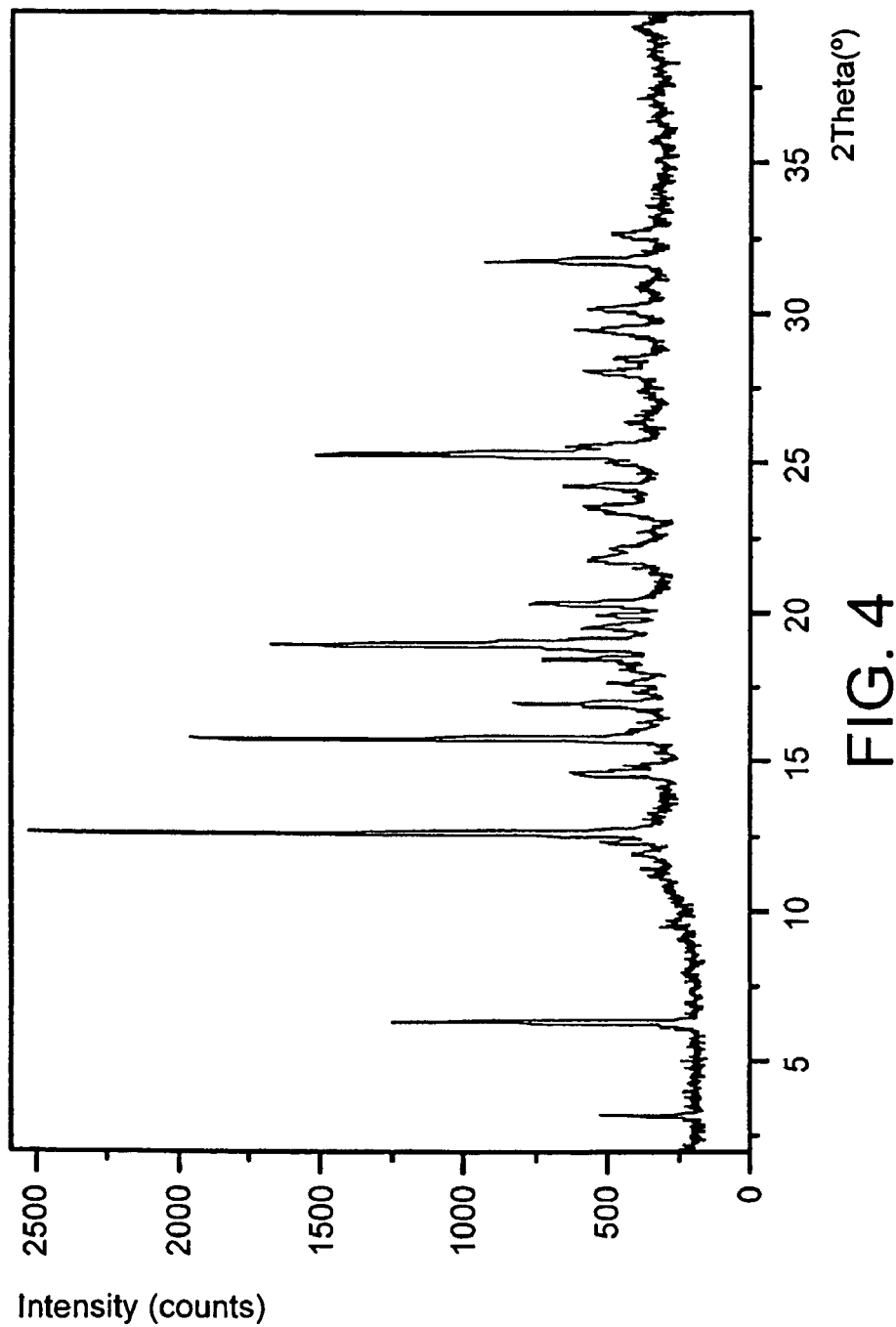
FIG. 4 shows an X-ray powder diffraction pattern of 4-{(1R)-2-[(6-{4-[3-(cyclopentylsulfonyl)phenyl]butoxy}hexyl)amino]-1-hydroxyethyl}-2-(hydroxymethyl)phenol 4-bromobenzene sulfonate.

The XRPD pattern of this product is given in FIG. 4.

iv) 4-{(1R)-2-[(6-{4-[3-(Cyclopentylsulfonyl)phenyl]butoxy}hexyl)amino]-1-hydroxyethyl}-2-(hydroxymethyl)phenol 3-toluene sulfonate This was prepared similarly to example 18 (ii) above to give crystals of the title compound. δ(DMSO-d$_6$) 9.40 (1H, br s), 8.35 (2H, v br s), 7.72-7.67 (2H, m), 7.58-7.55 (2H, m), 7.42 (1H, br s), 7.38 (1H, br d, J 7 Hz), 7.33 (1H, d, J 2 Hz), 7.18 (1H, t, J 7 Hz), 7.10 (1H, br d, J 7 Hz), 7.04 (1H, dd, J 2,8 Hz), 6.75 (1H, d, J 8 Hz), 5.95 (1H, br s), 5.02 (1H, t, J 5 Hz)), 4.76 (1H, br d, J 10 Hz), 4.48 (2H, d, J 5 Hz), 3.75 (1H, m), 3.38-3.28 (4H, partially obscured 2t), 3.06-2.88 (4H, 2m), 2.70 (2H, t, J 7 Hz), 2.29 (3H, s) 1.90-1.27 (20H, m).

Figure 5:
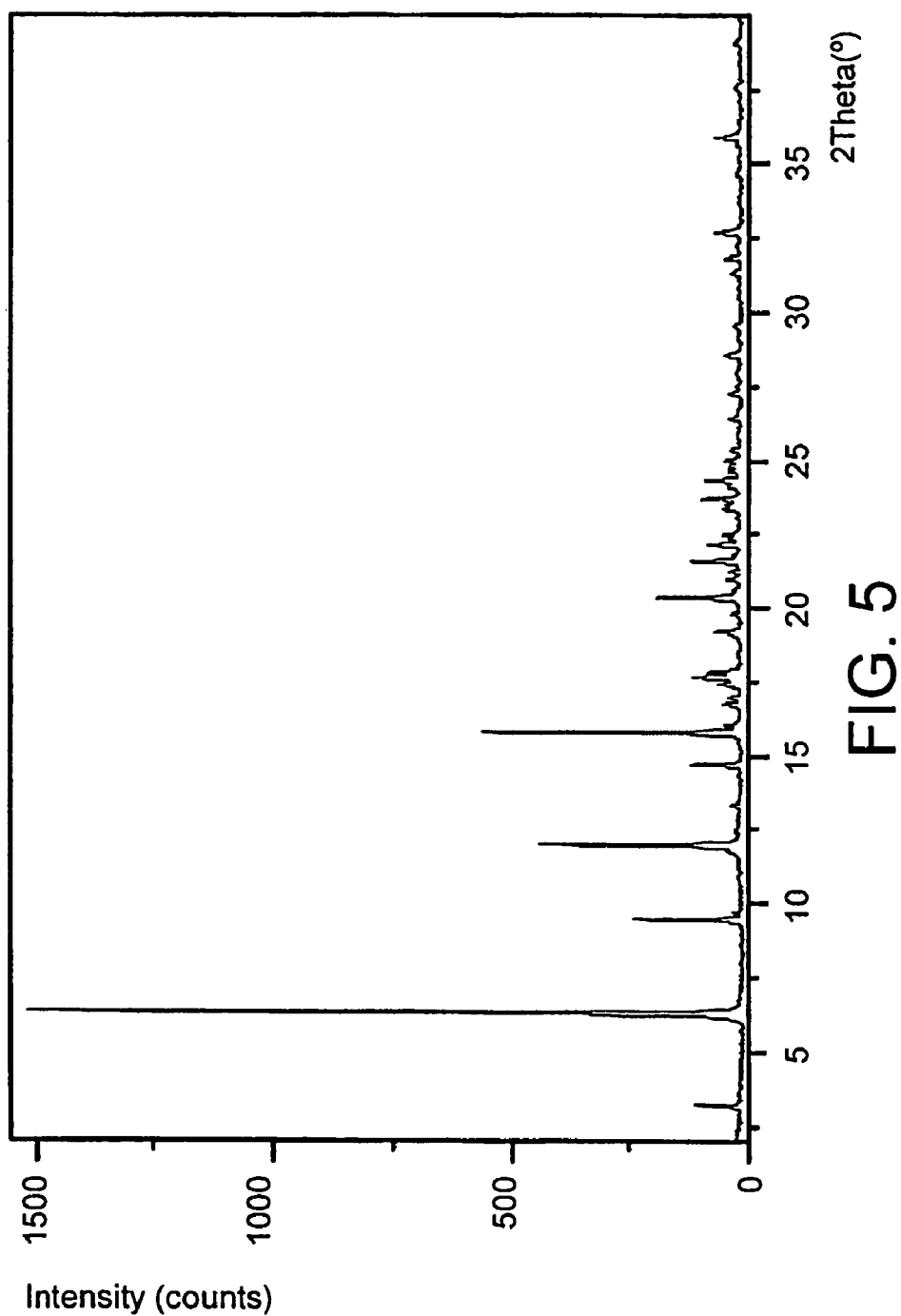
FIG. 5 shows an X-ray powder diffraction pattern of 4-{(1R)-2-[(6-{4-[3-(cyclopentylsulfonyl)phenyl]butoxy}hexyl)amino]-1-hydroxyethyl}-2-(hydroxymethyl)phenol 3-toluene sulfonate.

The XRPD pattern of this product is given in FIG. 5.

(v) 4-{(1R)-2-[(6-{4-[3-(Cyclopentylsulfonyl)phenyl]butoxy}hexyl)amino]-1-hydroxyethyl}-2-(hydroxymethyl)phenol 4-biphenyl sulfonate This was prepared similarly to example 18 (ii) above to give crystals of the title compound. δ (DMSO-d$_6$) 9.31 (1H, br s), 7.72-7.64 (6H, m), 7.61 (2H, m), 7.58-7.54 (2H, m), 7.46 (2H, br t, J 7 Hz), 7.36 (1H, ft, J 1,7 Hz), 7.30 (1H, d, J 1 Hz), 7.03 (1H, dd, J 1,8 Hz), 6.73 (1H, d, J 8 Hz), 5.70 (1H, br s), 4.97 (1H, t, J 5 Hz)), 4.75 (1H, m), 4.48 (2H, d, J 5 Hz), 3.78 (1H m), 3.40-3.20 (4H, partially obscured 2t), 2.98-2.80 (4H, 2m), 2.70 (2H, t, J 7 Hz), 1.90-1.22 (20H, m).

Figure 2:
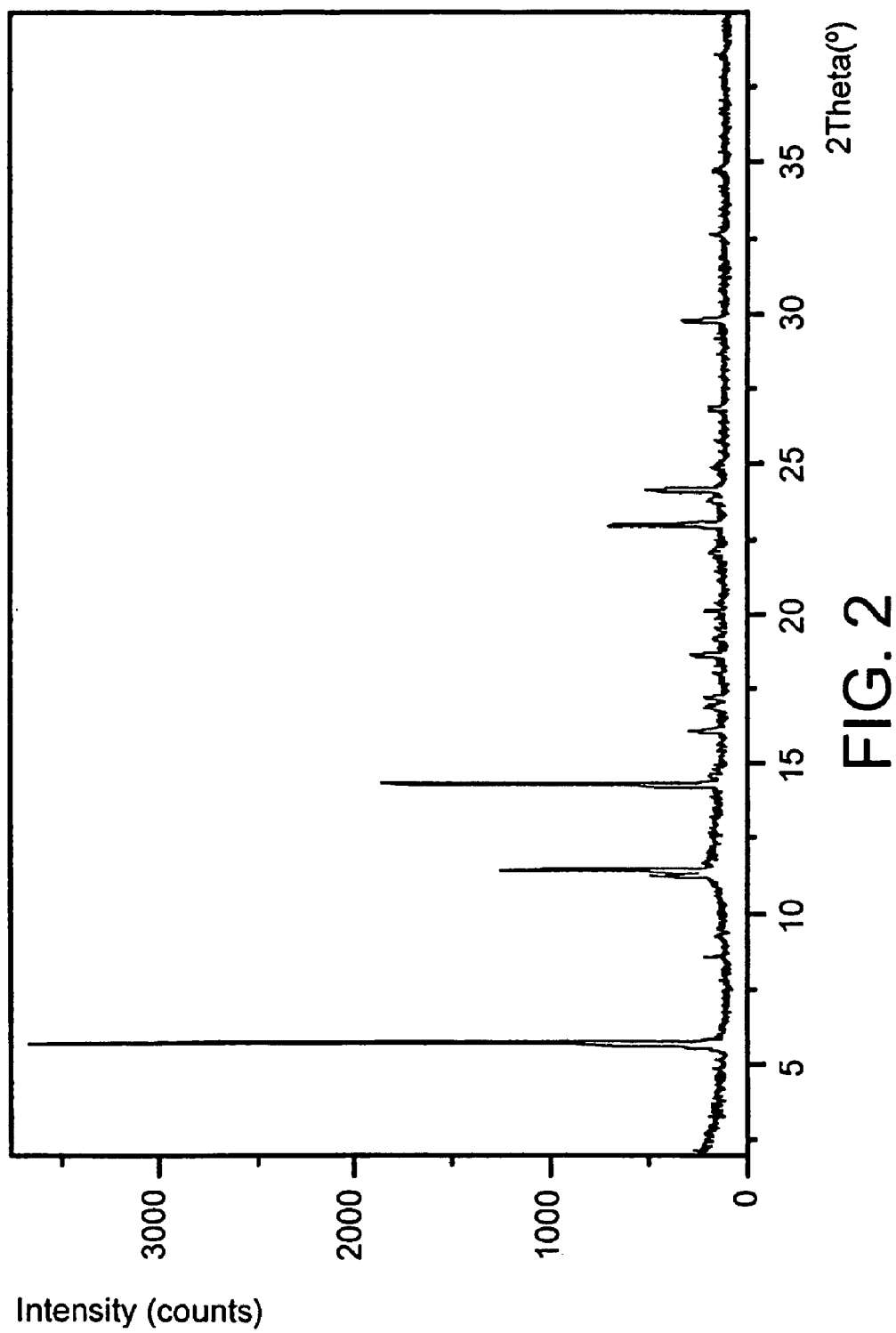
FIG. 2 shows an X-ray powder diffraction pattern of 4-{(1R)-2-[(6-{4-[3-(cyclopentylsulfonyl)phenyl]butoxy}hexyl)amino]-1-hydroxyethyl}-2-(hydroxymethyl)phenol 4-biphenyl sulfonate.

The XRPD pattern of this product is shown in FIG. 2.

Biological Activity

In vitro measurements of compound potency and intrinsic activity at the human Beta 1, 2 and 3 receptor.

Method 1

The potencies of the compounds of Examples 1-4 were determined using frog melanophores transfected with the human beta 2 adrenoreceptor. The cells were incubated with melatonin to induce pigment aggregation. Pigment dispersal was induced by compounds acting on the human beta 2 adrenoreceptor. The beta 2 agonist activity of test compounds was assessed by their ability to induce a change in light transmittance across a melanophore monolayer (a consequence of pigment dispersal). At the human beta 2 adrenoreceptor, compounds of said examples had IC$_{50}$ values below 1 μM.

Method 2

Potency of compounds of the invention at the human beta 2, 1 and 3 receptors was also determined using Chinese hamster ovary cells co-expressing the human receptor with a reporter gene. Studies were performed using either whole cells or membranes derived from those cells.

The three beta-receptors are coupled via the Gs G-protein to cause a stimulation of adenylate cyclase resulting in increased levels of cAMP in the cell. For direct cAMP measurements either membranes or frozen cells have been used with either the HitHunter enzyme fragment complementabon kit (DiscoveRx) or the Fp$^2$ fluorescence polarisation kit (Perkin Elmer) to quantify the levels of cAMP present. These assays provide a measure of agonist potency and intrinsic activity of the compounds at the various receptors.

The reporter gene in the cells has also been used to quantify potency at the beta 1 and 3 receptors. This is a reporter of cAMP levels using the cAMP response element upstream of a firefly luciferase gene. After stimulation of the receptor with an agonist an increase in the level of luciferase is measured as a quantification of the level of cAMP in the cell.

In this assay the potency of compounds at the human beta-2 receptor is expressed as a pEC$_{50}$ value. Compounds of Examples 2-9 and 11-15 had a pEC$_{50}$ of >6.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims.

What is claimed is:

1. A compound of formula (I):

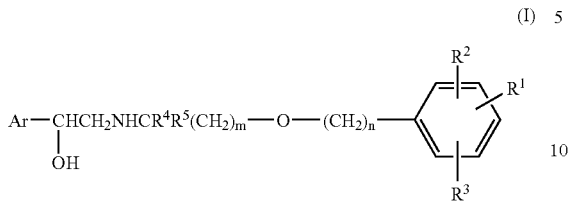

or a salt, solvate, or physiologically functional derivative thereof, wherein:

m is an integer of from 2 to 8; and
n is an integer of from 3 to 11;
with the proviso that m+n is 5 to 19;
$R^1$ is $SR^6$, $SOR^6$, or $SO_2R^6$,
wherein $R^6$ is a $C_{3-7}$cycloalkyl or $C_{3-7}$cycloalkenyl group;
$R^2$ and $R^3$ are independently selected from hydrogen, $C_{1-6}$alkyl, $C_{1-6}$alkoxy, halo, phenyl, and $C_{1-6}$haloalkyl;
$R^4$ and $R^5$ are independently selected from hydrogen and $C_{1-4}$alkyl with the proviso that the total number of carbon atoms in $R^4$ and $R^5$ is not more than 4;
Ar is a group selected from (a) 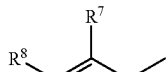

(b) 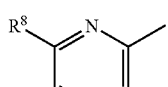

(c) 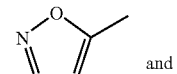

(d) 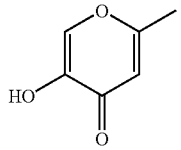

wherein $R^8$ represents hydrogen, halogen, —$(CH_2)_qOR^{11}$, —$NR^{11}C(O)R^{12}$, —$NR^{11}SO_2R^{12}$, —$SO_2NR^{11}R^{12}$, —$NR^{11}R^{12}$, —$OC(O)R^{13}$ or $OC(O)NR^{11}R^{12}$,
and $R^7$ represents hydrogen, halogen, or $C_{1-4}$ alkyl;
or $R^8$ represents —$NHR^{14}$ and $R^7$ and —$NHR^{14}$ together form a 5- or 6-membered heterocyclic ring;
$R^9$ represents hydrogen, halogen, —$OR^{11}$ or —$NR^{11}R^{12}$;
$R^{10}$ represents hydrogen, halogen, halo$C_{1-4}$ alkyl, —$OR^{11}$, —$NR^{11}R^{12}$, —$OC(O)R^{13}$ or $OC(O)NR^{11}R^{12}$;

$R^{11}$ and $R^{12}$ each independently represents hydrogen or $C_{1-4}$ alkyl, or in the groups —$NR^{11}R^{12}$, —$SO_2NR^{11}R^{12}$ and —$OC(O)NR^{11}R^{12}$, $R^{11}$ and $R^{12}$ independently represent hydrogen or $C_{1-4}$ alkyl or together with the nitrogen atom to which they are attached form a 5-, 6- or 7-membered nitrogen-containing ring,
$R^{13}$ represents an aryl group which may be unsubstituted or substituted by one or more substituents selected from halogen, $C_{1-4}$ alkyl, hydroxy, $C_{1-4}$ alkoxy or halo $C_{1-4}$ alkyl; and
q is zero or an integer from 1 to 4.

2. A compound according to claim 1 wherein $R^8$ is selected from the group consisting of halogen, —$(CH_2)_qOR^{11}$, —$NR^{11}C(O)R^{12}$, —$NR^{11}SO_2R^{12}$, —$SO_2NR^{11}R^{12}$, —$NR^{11}R^{12}$, —$OC(O)R^{13}$, $OC(O)NR^{11}R^{12}$, and —$NHR^{14}$ and $R^7$ and —$NHR^{14}$ together form a 5- or 6-membered heterocyclic ring.

3. A compound according to claim 1 wherein $R^1$ represents —$SO_2R^6$.

4. A compound according to claim 1 wherein $R^6$ represents a $C_{3-7}$ cycloalkyl group.

5. A compound according to claim 1 wherein $R^2$ and $R^3$ each represent hydrogen.

6. A compound according to claim 1 wherein $R^4$ and $R^5$ are independently selected from hydrogen and methyl.

7. A compound according to claim 1 wherein Ar is selected from a group (a) or (b):

(a) 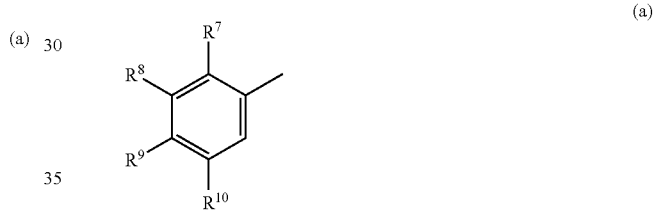

(b) 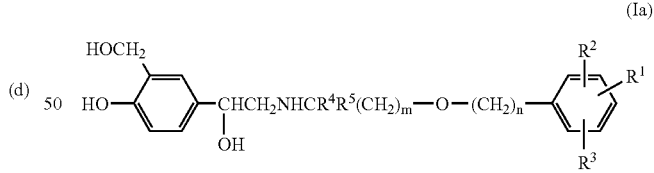

8. A compound of formula (Ia):

(Ia)

HOCH$_2$

HO—⟨phenyl⟩—CHCH$_2$NHCR$^4$R$^5$(CH$_2$)$_m$—O—(CH$_2$)$_n$—⟨phenyl: R$^2$, R$^1$, R$^3$⟩
        |
        OH or a salt, solvate, or physiologically functional derivative thereof, wherein:

m is an integer of from 2 to 8; and
n is an integer of from 3 to 11;
with the proviso that m+n is 5 to 19;
$R^1$ is $SR^6$, $SOR^6$, or $SO_2R^6$,
wherein $R^6$ is a $C_{3-7}$cycloalkyl or $C_{3-7}$cycloalkenyl group;
$R^2$ and $R^3$ are independently selected from hydrogen, $C_{1-6}$alkyl, $C_{1-6}$alkoxy, halo, phenyl, and $C_{1-6}$haloalkyl; and
$R^4$ and $R^5$ are independently selected from hydrogen and $C_{1-4}$alkyl with the proviso that the total number of carbon atoms in $R^4$ and $R^5$ is not more than 4.

9. A compound according to claim 1 wherein m is 5 or 6 and n is 3 or 4.

10. A compound selected from the group consisting of:
   4-{(1R)-2-[(6-{4-[3-(Cyclopentylsulfinyl)phenyl]butoxy}hexyl)amino]-1-hydroxyethyl}-2-(hydroxymethyl)phenol;
   4-{(1R)-2-[(6-{4-[3-(Cyclopentylsulfinyl)phenyl]butoxy}hexyl)amino]-1-hydroxyethyl}-2-(hydroxymethyl)phenol (Isomer 1);
   4-{(1R)-2-[(6-{4-[3-(Cyclopentylsulfinyl)phenyl]butoxy}hexyl)amino]-1-hydroxyethyl}-2-(hydroxymethyl)phenol (Isomer 2);
   4-{(1R)-2-[(6-{4-[3-(Cyclopentylsulfonyl)phenyl]butoxy}hexyl)amino]-1-hydroxyethyl}-2-(hydroxymethyl)phenol;
   4-{(1R)-2-[(6-{4-[4-(Cyclopentylsulfonyl)phenyl]butoxy}hexyl)amino]-1-hydroxyethyl}-2-(hydroxymethyl)phenol;
   4-((1R)-2-{[6-({4-[3-(Cyclohexylsulfonyl)phenyl]butyl}oxy)hexyl]amino}-1-hydroxyethyl)-2-(hydroxymethyl)phenol;
   4-((1R)-2-{[6-({4-[3-(3-Cyclopenten-1-ylsulfonyl)phenyl]butyl}oxy)hexyl]amino}-1-hydroxyethyl)-2-(hydroxymethyl)phenol;
   4-((1R)-2-{[6-({5-[3-(Cyclopentylsulfonyl)phenyl]pentyl}oxy)hexyl]amino}-1-hydroxyethyl)-2-(hydroxymethyl)phenol;
   4-((1R)-2-{[7-({3-[3-(Cyclopentylsulfonyl)phenyl]propyl}oxy)heptyl]amino}-1-hydroxyethyl)-2-(hydroxymethyl)phenol;
   4-((1R)-2-{[6-({4-[3-(Cyclopentylsulfonyl)-5-methylphenyl]butyl}oxy)hexyl]amino}-1-hydroxyethyl)-2-(hydroxymethyl)phenol;
   N-[5-((1R)-2-{[6-({4-[3-(Cyclopentylsulfonyl)phenyl]butyl}oxy)hexyl]amino}-1-hydroxyethyl)-2-hydroxyphenyl]methanesulfonamide;
   4-((1R)-2-{[6-({4-[3-(Cyclopentylsulfonyl)phenyl]butyl}oxy)hexyl]amino}-1-hydroxyethyl)-2-fluorophenol;
   6-{2-[(6-{4-[3-(Cyclopentylsulfonyl)phenyl]butoxy}hexyl)amino]-1-hydroxyethyl}-2-(hydroxymethyl)pyridin-3-ol;
   5-{(1R)-2-[(6-{4-[3-(Cyclopentylsulfonyl)phenyl]butoxy}hexyl)amino]-1-hydroxyethyl}-8-hydroxy-3,4-dihydroquinolin-2(1H)-one;
   5-{(1R)-2-[(6-{4-[3-(Cyclopentylsulfonyl)phenyl]butoxy}hexyl)amino]-1-hydroxyethyl}-2-hydroxyphenylformamide;
   salts thereof, solvates thereof, and physiologically functional derivatives thereof.

11. A compound according to claim 10 which is:
   4-{(1R)-2-[(6-{4-[3-(Cyclopentylsulfonyl)phenyl]butoxy}hexyl)amino]-1-hydroxyethyl}-2-(hydroxymethyl)phenol;
   or a salt, solvate, or physiologically functional derivative thereof.

12. A compound according to claim 1 in the form of a salt formed with an arylsulphonic acid.

13. A compound according to claim 8 which is selected from the group consisting of:
   4-{(1R)-2-[(6-{4-[3-(cyclopentylsulfonyl)phenyl]butoxy}hexyl)amino]-1-hydroxyethyl}-2-(hydroxymethyl) phenol 4-methylbenzenesulfonate;
   4-{(1R)-2-[(6-{4-[3-(cyclopentylsulfonyl)phenyl]butoxy}hexyl)amino]-1-hydroxyethyl}-2-(hydroxymethyl)phenol 4-bromobenzene sulfonate;
   4-{(1R)-2-[(6-{4-[3-(cyclopentylsulfonyl)phenyl]butoxy}hexyl)amino]-1-hydroxyethyl}-2-(hydroxyethyl)phenol 4-chlorobenzene sulfonate
   4-{(1R)-2-[(6-{4-[3-(cyclopentylsulfonyl)phenyl]butoxy}hexyl)amino]-1-hydroxyethyl}-2-(hydroxymethyl)phenol 3-toluene sulfonate;
   4-{(1R)-2-[(6-{4-[3-(cyclopentylsulfonyl)phenyl]butoxy}hexyl)amino]-1-hydroxyethyl}-2-(hydroxymethyl) phenol 4-biphenyl sulfonate; and
   4-{(1R)-2-[(6-{4-[3-(cyclopentylsulfonyl)phenyl]butoxy}hexyl)amino]-1-hydroxyethyl}-2-(hydroxymethyl)phenol, naphthalene-2-sulfonate.

14. A compound according to claim 13 wherein the salt is in crystalline form.

15. A method for the treatment of a clinical condition in a mammal for which a selective $\beta_2$-adrenoreceptor agonist is indicated, which comprises administering a therapeutically effective amount of a compound of formula (I):

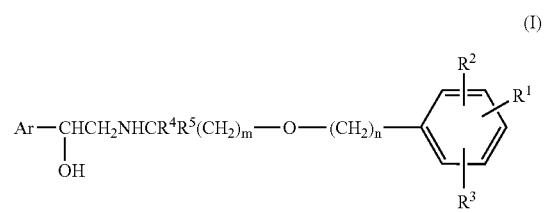

or a salt, solvate, or physiologically functional derivative thereof, wherein:
   m is an integer of from 2 to 8; and
   n is an integer of from 3 to 11;
   with the proviso that m+n is 5 to 19;
   $R^1$ is $SR^6$, $SOR^6$, or $SO_2R^6$,
   wherein $R^6$ is a $C_{3-7}$cycloalkyl or $C_{3-7}$cycloalkenyl group;
   $R^2$ and $R^3$ are independently selected from hydrogen, $C_{1-6}$alkyl, $C_{1-6}$alkoxy, halo, phenyl, and $C_{1-6}$haloalkyl;
   $R^4$ and $R^5$ are independently selected from hydrogen and $C_{1-4}$alkyl with the proviso that the total number of carbon atoms in $R^4$ and $R^5$ is not more than 4;
   Ar is a group selected from

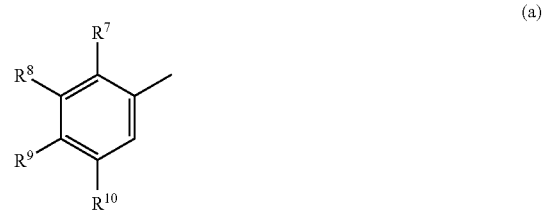

-continued

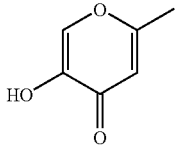

(d)

wherein $R^8$ represents hydrogen, halogen, $-(CH_2)_qOR^{11}$, $-NR^{11}C(O)R^{12}$, $-NR^{11}SO_2R^{12}$,
$-SO_2NR^{11}R^{12}$, $-NR^{11}R^{12}$, $-OC(O)R^{13}$ or $OC(O)NR^{11}R^{12}$, and $R^7$ represents hydrogen, halogen, or $C_{1-4}$ alkyl;

or $R^8$ represents $-NHR^{14}$ and $R^7$ and $-NHR^{14}$ together form a 5- or 6-membered heterocyclic ring;

$R^9$ represents hydrogen, halogen, $-OR^{11}$ or $-NR^{11}R^{12}$;

$R^{10}$ represents hydrogen, halogen, haloC$_{1-4}$alkyl, $-OR^{11}$, $NR^{11}R^{12}$, $-OC(O)R^{13}$ or $OC(O)NR^{11}R^{12}$;

$R^{11}$ and $R^{12}$ each independently represents hydrogen or $C_{1-4}$ alkyl, or in the groups $-NR^{11}R^{12}$, $-SO_2NR^{11}R^{12}$ and $-OC(O)NR^{11}R^{12}$, $R^{11}$ and $R^{12}$ independently represent hydrogen or $C_{1-4}$ alkyl or together with the nitrogen atom to which they are attached form a 5-, 6- or 7-membered nitrogen-containing ring, $R^{13}$ represents an aryl group which may be unsubstituted or substituted by one or more substituents selected from halogen, $C_{1-4}$ alkyl, hydroxy, $C_{1-4}$ alkoxy or halo $C_{1-4}$ alkyl; and q is zero or an integer from 1 to 4.

16. A pharmaceutical formulation comprising a compound of formula (I):

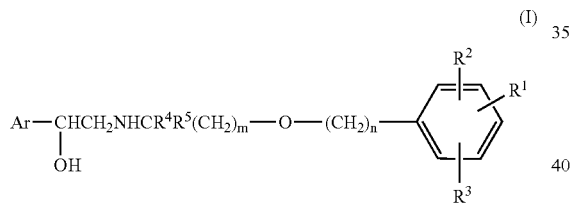

(I)

or a salt, solvate, or physiologically functional derivative thereof, wherein:

m is an integer of from 2 to 8; and n is an integer of from 3 to 11;

with the proviso that m+n is 5 to 19;

$R^1$ is $SR^6$, $SOR6$, or $SO_2 R^6$, wherein $R^6$ is a $C_{3-7}$cycloalkyl or $C_{3-7}$cycloalkenyl group;

$R^2$ and $R^3$ are independently selected from hydrogen, $C_{1-6}$alkyl, $C_{1-6}$alkoxy, halo phenyl, and $C_{1-6}$haloalkyl;

$R^4$ and $R^5$ are independently selected from hydrogen and $C_{1-4}$alkyl with the proviso that the total number of carbon atoms in $R^4$ and $R^5$ is not more than 4;

Ar is a group selected from

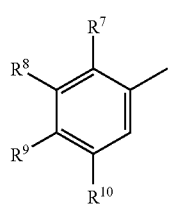

(a)

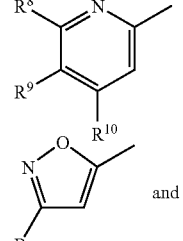

(b)

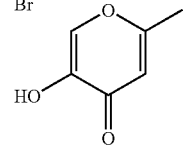

(c)

and

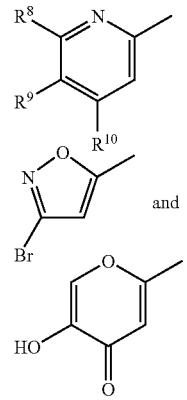

(d)

wherein $R^8$ represents hydrogen, halogen, $-(CH_2)_qOR^{11}$, $-NR^{11}C(O)R^{12}$, $-NR^{11}SO_2R^{12}$,
$-SO_2NR^{11}R^{12}$, $-NR^{11}R^{12}$, $-OC(O)R^{13}$ or $OC(O)NR^{11}R^{12}$, and $R^7$ represents hydrogen, halogen, or $C_{1-4}$ alkyl;

or $R^8$ represents $-NHR^{14}$ and $R^7$ and $-NHR^{14}$ together form a 5- or 6-membered heterocyclic ring;

$R^9$ represents hydrogen, halogen, $-OR^{11}$ or $-NR^{11}R^{12}$;

$R^{10}$ represents hydrogen, halogen, haloC$_{1-4}$alkyl, $-OR^{11}$, $-NR^{11}R^{12}$, $-OC(O)R^{13}$ or $OC(O)NR11R^{12}$;

$R^{11}$ and $R^{12}$ each independently represents hydrogen or $C_{1-4}$ alkyl, or in the groups $-NR^{11}R^{12}$, $-SO_2NR^{11}R^{12}$ and $-OC(O)NR^{11}R^{12}$, $R^{11}$ and $R^{12}$ independently represent hydrogen or $C_{1-4}$ alkyl or together with the nitrogen atom to which they are attached form a 5-, 6- or 7-membered nitrogen-containing ring, $R^{13}$ represents an aryl group which may be unsubstituted or substituted by one or more substituents selected from halogen, $C_{1-4}$ alkyl, Hydroxy, $C_{1-4}$ alkoxy or halo $C_{1-4}$ alkyl; and q is zero or an integer from 1 to 4, and a pharmaceutically acceptable carrier or excipient, and optionally one or more other therapeutic ingredients.

17. A combination comprising a compound of formula (I):

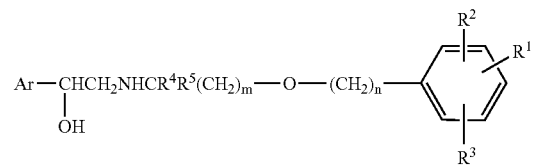

(I)

or a salt, solvate, or physiologically functional derivative thereof, wherein:

m is an integer of from 2 to 8; and n is an integer of from 3 to 11;

with the proviso that m+n is 5 to 19;

$R^1$ is $SR^6$, $SOR^6$, or $SO_2R^6$, wherein $R^6$ is a $C_{3-7}$cycloalkyl or $C_{3-7}$cycloalkenyl group;

$R^2$ and $R^3$ are independently selected from hydrogen, $C_{1-6}$alkyl, $C_{1-6}$alkoxy, halo, phenyl, and $C_{1-6}$haloalkyl;

$R^4$ and $R^5$ are independently selected from hydrogen and $C_{1-4}$alkyl with the proviso that the total number of carbon atoms in $R^4$ and $R^5$ is not more than 4;

Ar is a group selected from

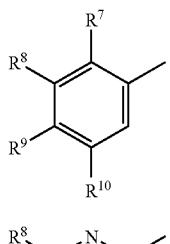
(a)

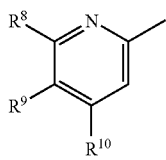
(b)

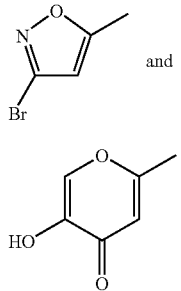
and
(c)

(d)

wherein R⁸ represents hydrogen, halogen, —(CH$_2$)$_q$OR$^{11}$, —NR$^{11}$C(O)R$^{12}$, —NR$^{11}$SO$_2$R$^{12}$, —SO$_2$NR$^{11}$R$^{12}$, —NR$^{11}$R$^{12}$, —OC(O)R$^{13}$ or OC(O)NR$^{11}$R$^{12}$, and R$^7$ represents hydrogen, halogen, or C$_{1-4}$ alkyl;

or R$^8$ represents —NHR$^{14}$ and R$^7$ and —NHR$^{14}$ together form a 5- or 6-membered heterocyclic ring;

R$^9$ represents hydrogen, halogen, —OR$^{11}$ or NR$^{11}$R$^{12}$;

R$^{10}$ rerpresents hydrogen, halogen, haloC$_{1-4}$ alkyl, —OR$^{11}$, —NR$^{11}$R$^{12}$, —OC(O)R$^{13}$ or OC(O)NR$^{11}$R$^{12}$;

R$^{11}$ and R$^{12}$ each independently represents hydrogen or C$_{1-4}$ alkyl, or in the groups —NR$^{11}$R$^{12}$, —SO$_2$NR$^{11}$R$^{12}$ and —OC(O)NR$^{11}$R$^{12}$, R$^{11}$ and R$^{12}$ independently represent hydrogen or C$_{1-4}$ alkyl or together with the nitrogen atom to which they are attached form a 5-, 6- or 7-membered nitrogen-containing ring, R$^{13}$ represents an aryl group which may be unsubstituted or substituted by one or more substituents selected from halogen, C$_{1-4}$ alkyl, hydroxy, C$_{1-4}$ alkoxy or halo C$_{1-4}$ alkyl; and q is zero or an integer from 1 to 4 or a pharmaceutically acceptable salt, solvate, or physiologically functional derivative thereof, and one or more other therapeutic ingredients.

18. A compound according to claim 1, wherein R$^{13}$ is a phenyl group.

19. A compound according to claim 1, wherein R$^{13}$ is a naphthyl group.

20. A method according to claim 15, wherein the mammal is a human.

21. A method according to claim 15, wherein the clinical condition is asthma.

22. A method according to claim 15, wherein the clinical condition is COPD.

* * * * *